(12) United States Patent
Low et al.

(10) Patent No.: US 9,731,035 B2
(45) Date of Patent: Aug. 15, 2017

(54) METHOD OF IMAGING OSTEOARTHRITIS USING A FOLATE CONJUGATE

(71) Applicant: Purdue Research Foundation, West Lafayette, IN (US)

(72) Inventors: Philip S. Low, West Lafayette, IN (US); Andrew R. Hilgenbrink, Nashville, TN (US)

(73) Assignee: Purdue Research Foundation, West Lafayette, IN (US)

( * ) Notice: Subject to any disclaimer, the term of this patent is extended or adjusted under 35 U.S.C. 154(b) by 741 days.

(21) Appl. No.: 13/793,654

(22) Filed: Mar. 11, 2013

(65) Prior Publication Data

US 2014/0065066 A1  Mar. 6, 2014

Related U.S. Application Data

(63) Continuation of application No. 12/391,981, filed on Feb. 24, 2009, now abandoned, which is a continuation of application No. 11/481,264, filed on Jul. 5, 2006, now abandoned.

(60) Provisional application No. 60/696,740, filed on Jul. 5, 2005, provisional application No. 60/801,636, filed on May 18, 2006.

(51) Int. Cl.
| | |
|---|---|
| *A61K 51/04* | (2006.01) |
| *A61K 49/00* | (2006.01) |
| *A61K 38/19* | (2006.01) |
| *A61K 47/48* | (2006.01) |
| *A61K 38/47* | (2006.01) |
| *C09B 11/24* | (2006.01) |

(52) U.S. Cl.
CPC ............ *A61K 51/044* (2013.01); *A61K 38/19* (2013.01); *A61K 38/47* (2013.01); *A61K 47/48061* (2013.01); *A61K 47/48107* (2013.01); *A61K 47/48246* (2013.01); *A61K 47/48815* (2013.01); *A61K 49/0021* (2013.01); *A61K 49/0041* (2013.01); *A61K 49/0043* (2013.01); *A61K 49/0052* (2013.01); *A61K 51/0459* (2013.01); *C09B 11/24* (2013.01)

(58) Field of Classification Search
None
See application file for complete search history.

(56) References Cited

U.S. PATENT DOCUMENTS

| | | | |
|---|---|---|---|
| 2,816,110 A | 12/1957 | Sletzinger et al. | |
| 4,577,636 A | 3/1986 | Spears | |
| 4,641,650 A | 2/1987 | Mok | |
| 4,713,249 A | 12/1987 | Schroder | |
| 4,718,417 A | 1/1988 | Kittrell et al. | |
| 4,785,806 A | 11/1988 | Deckelbaum | |
| 4,817,601 A | 4/1989 | Roth et al. | |
| 4,850,351 A | 7/1989 | Herman et al. | |
| 4,917,084 A | 4/1990 | Sinofsky | |
| 4,950,266 A | 8/1990 | Sinofsky | |
| 5,057,540 A | 10/1991 | Kensil et al. | |
| 5,094,848 A | 3/1992 | Brixner | |
| 5,108,921 A | 4/1992 | Low et al. | |
| 5,140,104 A | 8/1992 | Coughlin et al. | |
| 5,192,525 A | 3/1993 | Yang et al. | |
| 5,217,456 A | 6/1993 | Narciso | |
| 5,266,333 A | 11/1993 | Cady et al. | |
| 5,275,594 A | 1/1994 | Baker et al. | |
| 5,336,506 A | 8/1994 | Josephson et al. | |
| 5,373,093 A | 12/1994 | Vallarino et al. | |
| 5,399,338 A | 3/1995 | Born et al. | |
| 5,416,016 A | 5/1995 | Low et al. | |
| 5,417,982 A | 5/1995 | Modi | |
| 5,547,668 A | 8/1996 | Kranz et al. | |
| 5,552,545 A | 9/1996 | Pearce et al. | |
| 5,562,100 A | 10/1996 | Kittrell et al. | |
| 5,576,305 A | 11/1996 | Ratcliffe | |
| 5,688,488 A | 11/1997 | Low et al. | |
| 5,753,631 A | 5/1998 | Paulson et al. | |
| 5,759,546 A | 6/1998 | Weinberg et al. | |
| 5,820,847 A | 10/1998 | Low et al. | |
| 6,093,382 A | 7/2000 | Wedeking et al. | |
| 6,167,297 A | 12/2000 | Benaron | |
| 6,204,371 B1 | 3/2001 | Levinson | |
| 6,217,847 B1 | 4/2001 | Contag et al. | |

(Continued)

FOREIGN PATENT DOCUMENTS

| | | |
|---|---|---|
| CA | 2520406 | 10/2004 |
| CA | 2666234 | 5/2008 |

(Continued)

OTHER PUBLICATIONS

Etchebehere et al. (Semin Nucl Med Jan. 1998; 28(1):41-61).*

(Continued)

*Primary Examiner* — Sharon Wen
(74) *Attorney, Agent, or Firm* — Barnes & Thornburg LLP

(57) ABSTRACT

The invention relates to a method of treating or diagnosing a disease state mediated by monocytes. The method utilizes a composition comprising a conjugate or complex of the general formula $A_b\text{-}X$ wherein the group $A_b$ comprises a ligand that binds to monocytes, and when the conjugate is being used for treatment of the disease state, the group X comprises an immunogen, a cytotoxin, or a compound capable of altering monocyte function, and when the conjugate is being used for diagnosing the disease state, the group X comprises an imaging agent.

24 Claims, 7 Drawing Sheets

(56) References Cited

U.S. PATENT DOCUMENTS

| | | |
|---|---|---|
| 6,221,334 B1 | 4/2001 | Wedeking et al. |
| 6,246,901 B1 | 6/2001 | Benaron |
| 6,270,766 B1 | 8/2001 | Feldman et al. |
| 6,335,434 B1 | 1/2002 | Guzaev et al. |
| 6,365,362 B1 | 4/2002 | Terstappen et al. |
| 6,387,350 B2 | 5/2002 | Goldenberg |
| 6,507,747 B1 | 1/2003 | Gowda et al. |
| 6,780,984 B2 | 8/2004 | Wang et al. |
| 6,782,289 B1 | 8/2004 | Strauss |
| 6,915,154 B1 | 7/2005 | Docherty et al. |
| 6,960,449 B2 | 11/2005 | Wang et al. |
| 7,033,594 B2 | 4/2006 | Low et al. |
| 7,128,893 B2 | 10/2006 | Low et al. |
| 7,223,380 B2 | 5/2007 | Yang et al. |
| 7,381,535 B2 | 6/2008 | Perez et al. |
| 7,601,332 B2 | 10/2009 | Vlahov |
| 7,740,854 B2 | 6/2010 | Low et al. |
| 7,977,058 B2 | 7/2011 | Low et al. |
| 8,043,602 B2 | 10/2011 | Jallad et al. |
| 8,043,603 B2 | 10/2011 | Kennedy et al. |
| 8,383,354 B2 | 2/2013 | Low et al. |
| 8,388,977 B2 | 3/2013 | Low et al. |
| 8,586,595 B2 | 11/2013 | Low et al. |
| 8,685,752 B2 | 4/2014 | Low et al. |
| 8,795,633 B2 | 8/2014 | Low et al. |
| 2001/0031252 A1 | 10/2001 | Low et al. |
| 2002/0127181 A1 | 9/2002 | Edwards et al. |
| 2002/0192157 A1 | 12/2002 | Low et al. |
| 2003/0086900 A1 | 5/2003 | Low et al. |
| 2003/0162234 A1 | 8/2003 | Jallad et al. |
| 2003/0198643 A1 | 10/2003 | Lu |
| 2003/0219375 A1 | 11/2003 | Piwnica-Worms |
| 2004/0033195 A1 | 2/2004 | Leamon et al. |
| 2004/0057900 A1 | 3/2004 | Edwards et al. |
| 2004/0136910 A1 | 7/2004 | Kennedy et al. |
| 2004/0184990 A1 | 9/2004 | Larsen et al. |
| 2004/0242582 A1 | 12/2004 | Green et al. |
| 2005/0002942 A1 | 1/2005 | Vlahov et al. |
| 2005/0026866 A1 | 2/2005 | Pawelek |
| 2005/0164906 A1 | 7/2005 | Riccardi |
| 2005/0227985 A9 | 10/2005 | Green et al. |
| 2005/0244336 A1 | 11/2005 | Low |
| 2005/0261170 A1 | 11/2005 | Hansen et al. |
| 2006/0002891 A1 | 1/2006 | Pouletty |
| 2006/0067946 A1 | 3/2006 | Low et al. |
| 2006/0134002 A1 | 6/2006 | Lin |
| 2006/0182687 A1 | 8/2006 | Yang et al. |
| 2006/0204565 A1 | 9/2006 | Low et al. |
| 2007/0009434 A1 | 1/2007 | Low et al. |
| 2007/0031434 A1 | 2/2007 | Leamon et al. |
| 2007/0231266 A1 | 10/2007 | Low et al. |
| 2007/0276231 A1 | 11/2007 | Low et al. |
| 2008/0119475 A1 | 5/2008 | Low et al. |
| 2008/0138396 A1 | 6/2008 | Low et al. |
| 2008/0254499 A1 | 10/2008 | Low et al. |
| 2008/0311037 A1 | 12/2008 | Heston et al. |
| 2009/0012009 A1 | 1/2009 | Low et al. |
| 2010/0055735 A1 | 3/2010 | Low et al. |
| 2010/0092389 A1 | 4/2010 | Jaffer |
| 2010/0322854 A1 | 12/2010 | Low et al. |
| 2011/0044897 A1 | 2/2011 | Low et al. |
| 2012/0003151 A1 | 1/2012 | Low et al. |
| 2012/0276191 A1 | 11/2012 | Low et al. |
| 2012/0301397 A1 | 11/2012 | Low et al. |
| 2013/0101519 A1 | 4/2013 | Low et al. |
| 2013/0336895 A1 | 12/2013 | Kennedy et al. |
| 2013/0344002 A1 | 12/2013 | Jallad et al. |
| 2014/0056809 A1 | 2/2014 | Low et al. |
| 2014/0112866 A1 | 4/2014 | Low et al. |

FOREIGN PATENT DOCUMENTS

| | | |
|---|---|---|
| EP | 0220030 | 10/1986 |
| EP | 0273085 | 12/1986 |
| EP | 1548027 | 6/2005 |
| EP | 1940473 | 7/2008 |
| JP | 2774378 | 7/1998 |
| JP | 2004-530678 | 11/2002 |
| JP | 2003-515570 | 5/2003 |
| JP | 2005-519078 | 9/2003 |
| JP | 2003-534388 | 11/2003 |
| RU | 2123338 | 11/1996 |
| RU | 2101703 | 10/1998 |
| WO | 90/12096 | 10/1990 |
| WO | 91/19501 | 12/1991 |
| WO | 91/19502 | 12/1991 |
| WO | 92/13572 | 2/1992 |
| WO | WO94/07542 | 4/1994 |
| WO | 96/22521 | 7/1996 |
| WO | 96/36367 | 11/1996 |
| WO | 97/37690 | 10/1997 |
| WO | 98/49196 | 11/1998 |
| WO | WO98/58678 | 12/1998 |
| WO | 99/41285 | 8/1999 |
| WO | 00/73332 | 12/2000 |
| WO | 01/19320 | 3/2001 |
| WO | 01/39806 | 6/2001 |
| WO | 01/47552 | 7/2001 |
| WO | 01/74382 | 10/2001 |
| WO | 01/91807 | 12/2001 |
| WO | 02/087424 | 11/2002 |
| WO | WO 03/072091 | 9/2003 |
| WO | 2004/044227 | 5/2004 |
| WO | 2004/069159 | 8/2004 |
| WO | 2004/110250 | 12/2004 |
| WO | 2005/049579 | 6/2005 |
| WO | 2005/067644 | 7/2005 |
| WO | 2005/087275 | 9/2005 |
| WO | 2006/012527 | 2/2006 |
| WO | 2006/034046 | 3/2006 |
| WO | 2006/065943 | 6/2006 |
| WO | 2006/071754 | 7/2006 |
| WO | 2006/101845 | 9/2006 |
| WO | 2007/001466 | 1/2007 |
| WO | 2007/006041 | 1/2007 |
| WO | WO 2007/038346 | 4/2007 |
| WO | 2008/057437 | 5/2008 |
| WO | 2008/098112 | 8/2008 |
| WO | 2008/148001 | 12/2008 |
| WO | 2009/002993 | 12/2008 |
| WO | 2009/026177 | 2/2009 |

OTHER PUBLICATIONS

NCBI, MeSH definition for Indocarbocyanine Green, 2 pages, Aug. 31, 2008.

"Macrophages" from Wikipedia, updated Nov. 18, 2007.

Achilefu et al., "Novel Receptor-Targeted Fluorescent Contrast Agents for In Vivo Tumor Imaging", Investigative Radiology, vol. 35, No. 8, pp. 479-485, Aug. 2000.

Antohe et al., "Increased uptake of folate conjugates by activated macrophages in experimental hyperlipemia", Cell Tissue Research, vol. 320, No. 2, pp. 277-285, May 2005.

Aviram et al., "Intralipid infusion abolishes ability of human serum to cholesterol-load cultured macrophages", Arteriosclerosis, vol. 9, pp. 67-75, 1989.

Ballou et al., "Tumor labeling in vivo using cyanine-conjugated monoclonal antibodies", Cancer Immunol Immunother, vol. 41, pp. 257-263, 1995.

Barrera et al., "Synovial macrophage depletion with clodronate-containing liposomes in rheumatoid arthritis", Arthritis and Rheumatism, vol. 43, pp. 1951-1959, 2000.

Beaumont et al., "Selective Fluorodenitration of Chloronitroaromatics", J. Fluorine Chem., vol. 63, pp. 25-30, 1993.

Becker et al., "Macromolecular Contrast Agents for Optical Imaging of Tumors: Comparison of Indotricarbocyanine-labeled Human Serum Albumin and Transferrin", Photochemistry and Photobiology, vol. 72, No. 2, pp. 234-241, May 14, 2000.

U.S. Appl. No. 61/235,220, filed Aug. 19, 2009, Low et al.

U.S. Appl. No. 61/157,847, filed Mar. 5, 2009, Low et al.

(56) References Cited

OTHER PUBLICATIONS

Bettio et al, "Synthesis and Preclinical Evaluation of a Folic Acid Derivative Labeled with 18F for PET Imaging of Folate Receptor-Positive Tumors", The Journal of Nuclear Medicine, vol. 47, No. 7, pp. 1153-1160, 2006.
Bock et al., "Sulfonamide Structure-Activity Relationships in a Cell-Free System. 2. Proof for the Formation of a Sulfonamide-Containing Folate Analog", Journal of Medicinal Chemistry, vol. 17, No. 1, pp. 23-28, 1974.
Boechat et al., Fluorodenitrations Using Tetramethylammonium Fluoride, J. Soc. Chem, Commun., pp. 921-992, 1993.
Boente et al., "Screening, imaging, and Early Diagnosis of Ovarian Cancer", Clinical Obstetrics and Gynecology, vol. 37, No. 2, pp. 377-391, Jun. 1994.
Bonasera et al., "The Synthesis of [26, 27-11C]Dihydroxyvitamin D3, a Tracer for Positron Emission Tomography (PET), Bioorganic & Medicinal Chemistry", Elsevier Science Ltd., 2001, vol. 9, pp. 3123-3128.
Budinger et al., "New Approaches to Targeting Arthritis with Radiopharmaceuticals", The Journal of Rheumatology, 22(1) Supp: 62-67, 1995.
Burke et al., "Book Review. The Macrophage", British Journal of Cancer, vol. 89, p. 421, 2003.
Campbell et al., "Folate-binding Protein is a Marker for Ovarian Cancer", Cancer Research, vol. 51, pp. 5329-5338, Oct. 1991.
Canis et al., "Laparoscopic Diagnosis of Adnexal Cystic Masses: A 12-Year Experience With Long-Term Follow-Up", Obstetrics & Gynecology, vol. 83, No. 5, pp. 707-712, May 1994.
Case, "Ultrasound Physics and Instrumentation, Surgical Clinics of North America", vol. 78, No. 2, pp. 197-217, Apr. 1998.
Chen et al., "MicroPET Imaging of Brain Tumor Angiogenesis with 18F-Labeled PEGylated RGD Peptide", European Journal of Nuclear Medicine and Molecular Imaging, vol. 31, No. 8, pp. 1081-1089, Aug. 2004.
Tung et al., "Preparation of a Cathepsin D Sensitive Near-Infrared Fluorescence Probe for Imaging", American Chemical Society, vol. 10, No. 5, pp. 692-696, 1999.
Cochlovius, "Therapeutic Antibodies", Modern Drug Discovery, pp. 33-38, 2003.
Cohen et al., "Screening for ovarian cancer: The role of noninvasive imaging techniques", Am J. Obstet Gynecol., vol. 170, No. 4, pp. 1088-1094, 1994.
Cohen et al., "Three-Dimensional Power Doppler Ultrasound Improves the Diagnostic Accuracy for Ovarian Cancer Prediction", Gynecologic Oncology, vol. 82, pp. 40-48, 2001.
Cox et al., "Anhydrous, Tetrabutylammonium Fluoride: A Mild but Highly Efficient Source of Nucleophilic Fluoride Ion", J. Org. Chem., No. 49, pp. 3216-3219, 1984.
Degrado et al., "Synthesis and Evaluation of (18)F-Labeled Choline Analogs as Oncologic PET Tracers", J. Nuclear Medicine, vol. 42, No. 12, pp. 1805-1814, 2001.
DePriest et al., "Transvaginal Sonography as a Screening Method for the Detection of Early Ovarian Cancer", Gynecologic Oncology, vol. 65, No. GO974705, pp. 408-414, 1997.
U.S. Appl. No. 12/526,096, filed Aug. 6, 2009, Low et al.
Feldman et al., "Anti-TNFa Therapy Is Useful in Rheumatoid Arthritis and Crohn's Disease: Analysis of the Mechanism of Action Predicts Utility in Other Diseases", Transplant. Proc. , 30, pp. 4126-4127, 1998.
Forstner et al., "CT and MRI of ovarian cancer", Abdominal Imaging, vol. 20, pp. 2-8, 1995.
Garg et al., "Fluorine-18 Labeling of Monoclonal Antibodies and Fragments with Preservation of Immunoreactivity", Bioconjugate Chem., vol. 2, No. 1, pp. 44-49, 1991.
Giroldo et al., "An Unusually Fast Nucleophilic Aromatic Displacement Reaction: The Gas-Phase Reaction of Fluoride Ions with Nitrobenzene", Angew. Chem. Int. Ed., No. 43, pp. 3588-3590, 2004.
Godwin et al., "The synthesis of biologically active pteroyloligo-g-L-glutamates (folic acid conjugates): Evaluation of (3H) pteroylheptaglutamate for metabolic studies", Journal of Biological Chemistry. vol. 247, pp. 2266-2271, Apr. 1974.
Gotoh, "Causes and treatment of rheumatoid arthritis; recent trend I. Progress in pathogenesis of rheumatoid arthritis; role of macrophages and dendritic cells", Pharma Nedica, Japan Medical Review Co., Ltd., Tokyo, 17(10): 35-39, 1999.
Greenman, Y., et al., "Heterogeneous Expression of Two Somatostatin Receptor Subtypes in Pituitary Tumors," Journal of Clinical Endocrinology and Metabolism, vol. 78, No. 2, pp. 398-403, 1994.
Hamacher et al., "No-Carrier-Added Nucleophilic 18F-Lavelling in an Electrochemical Cell Exemplified by the Routine Production of [18F]altanserin", Applied Radiation and Isotopes, No. 64, pp. 989-994, 2006.
Harris et al., "Human leukemic models of myelomonocytic development: a review of the HL-60 and U937 cell lines", Journal of Leukocyte Biology, vol. 37., No. 4, pp. 407-422, 1985.
Holmgren et al., "Strategies for the Induction of Immune Responses at Mucosal Surfaces Making Use of Cholera Toxin B Subunit As Immunogen, Carrier, and Adjuvant", Am. J. Trop Med Hyd, 50, pp. 42-54, 1994.
Hynes et al., "Quinazolines as Inhibitors of Dihydrofolate Reductase. 4. Classical Analogues of Folic and Isofolic Acids", Journal of Medicinal Chemistry, vol. 20, No. 4, pp. 588-591, 1977.
Jager et al., "Resection guided by antibodies (REGAJ): a diagnostic procedure during second-look operation in ovarian cancer patients", Depts of Obstetrics, Gynecology and Nuclear Medicine, Univ of Erlangen-Nurnberg, pp. 18-20, 1990.
Johnstrom et al., "18F-Endothelin-1, a Positron Emission Tomography (PET) Radioligand for the Endothelin Receptor System: Radiosynthesis and In Vivo Imaging Using MicroPET", Clinical Science, vol. 103, Suppl. 48, pp. 45-85, 2002.
Karlan, "The Status of Ultrasound and Color Doppler Imaging for the Early Detection of Ovarian Cancer", Cancer Investigation, vol. 15, No. 3, pp. 265-269, 1997.
Karlan et al., "Ovarian Cancer Screening: The Role of Ultrasound in Early Detection", Cancer Supplement, vol. 76, No. 10, pp. 2011-2015, Nov. 1995.
Karsten et al., "Towards Usage-Based Accounting: Applying Policy-Based Intelligent Agents, ITC 15". Elsevier Science B.V., pp. 633-642, 1997.
Kennedy et al., "Evaluation of Folate Conjugate Uptake and Transport by the Choroid Plexus of Mice", Pharmaceutical Research, vol. 20, No. 5, p. 714-719, May 2003.
Kennedy et al., "Optical imaging of metastatic tumors using a folate-targeted fluorescent probe", J. of Biomedical Optics, vol. 8, No. 4, pp. 636-641, Oct. 2003.
Kim et al., "Synthesis and Biological Activity of 10-Thia-10-deaza Analogs of Folic Acid, Pteroic Acid, and Related Compounds", Journal of Medicinal Chemistry, vol. 18, No. 8, pp. 776-780, 1975.
Kinne et al., "Macrophage in rheumatoid arthritis", Arthritis Research , vol. 2, No. 3, pp. 189-202, 2000.
Konda et al., "Development of a Tumor-Targeting MR Contrast Agent Using the High-Affinity Folate Receptor", Investigative Radiology, vol. 35, No. 1, pp. 50-57, 2000.
Kramer, "Basic Principles of Magnetic Resonance Imaging", Radiological Clinics of North America, vol. 22, No. 4, pp. 765-778, Dec. 1984.
Kuroiwa et al., "Development of a Fluorescein Operative Microscope for Use During Malignant Glioma Surgery", Elsevier Science Inc., vol. 50, pp. 41-49, 1998.
Leamon et al., "Folate-mediated targeting: from diagnosis to drug and gene therapy", DDT vol. 6 No. 1 44-51, Jan. 2001.
Leamon et al., "Synthesis and Biological Evaluation of EC140: A Novel Folate-Targeted Cinca Alkaloid Conjugate", Bioconjugate Chem., vol. 17, No. 5, pp. 1226-1232, 2006.
Leamon et al., "Synthesis and Biologicial Evaluation of EC20: A New Folate-Derived, 99mTc-Based Radiopharmaceutical", Bioconjugate Chemistry, vol. 13, No. 6, pp. 1200-1210, 2002.
Leamon et al., "Selective Targeting of Malignant Cells with Cytotoxin-Folate Conjugates", J. Drug Targeting 2: 101-112, 1994.
Lee et al., "Folic Acid Antagonists. Methotrexate Analogs Containing Spurious Amino Acids. Dichlorohomofolic Acid", Journal of Medicinal Chemistry, vol. 17, No. 3, pp. 326-330, 1974.

(56) References Cited

OTHER PUBLICATIONS

Lemaire et al., "Fluorine-18-Altanserin: A Radioligand for the Study of Serotonin Receptors with PET: Radiolabeling and In Vivo Biologic Behavior in Rats", The Journal of Nuclear Medicine. vol. 32, No. 12, pp. 2266-2272, Dec. 1991.
Licha et al., "Hydrophilic Cyanine Dyes as Contrast Agents for Near-infrared Tumor Imaging: Synthesis, Photophysical Properties and Spectroscopic In vivo Characterization", Photochemistry and Photobiology, vol. 72, No. 3, pp. 392-398, 2000.
Liotta et al., "The Chemistry of "Naked" Anions. I. Reactions of the 18-Crown-6 Complex of Potassium Fluoride with Organic Substrates in Aprotic Organic Solvents", Journal of American Chemical Society, vol. 96, No. 7, pp. 2250-2252, Apr. 3, 1974.
Liu-Wu et al., "Identification and Analysis of Macrophage-Derived Foam Cells from Human Atherosclerotic Lesions by Using a 'Mock' FL3 Channel in Flow Cytometry", Cytometry, vol. 29, No. 2, pp. 155-164, 1997.
Low et al., "Ovarian Cancer: Comparison of findings with Perfluorocarbon-enhanced MR Imaging, In-111-CYT-103 Immunoscintigraphy, and CT", Depts of Diagnostic Rad and Onc, Sharp Memorial Hospital, vol. 195, No. 2, pp. 391-400, 1995.
Lu et al., "Folate-Targeted Enzyme Prodrug Cancer Therapy Utilizing Penicillin-V Amidase and a Doxorubicin Prodrug", J. Drug Targeting 7:43-53, 1999.
Mahmood et al, "Near Infrared Optical Imaging for Protease Activity for Tumor Detection", Radiology, 213:866-870, 1999.
Maiman et al., "Laproscopic Excision of Ovarian Neoplasm Subsequently Found to Be Malignant", Obstetrics & Gynecology, vol. 77, No. 4, pp. 563-565, Apr. 1991.
U.S. Appl. No. 60/956,489, filed Aug. 17, 2007, Low et al.
Mancini et al., "Relative contributions of apolipoprotein a and apolipoprotein B to the development of fatty lesions in the proximal aorta of mice", Arterioscler. Thromb. Vasc. Biol., vol. 15, pp. 1911-1916, 1995.
Mantovani et al., "Folate Binding Protein Distribution in Normal Tissues and Biological Fluids From Ovarian Carcinoma Patients as Detected by the Monoclonal Antibodies Mov 18 and Mov 19", European Journal of Cancer, vol. 30A, No. 3, pp. 363-369, 1994.
Mathias et al., "Preparation of 66Ga- and 68GA-labeled GA(III)-deferoxamine-folate as potential folate-receptor-targeted PET radiopharmaceuticals", Nuclear Medicine and Biology, vol. 30, pp. 725-731, 2003.
Matsuyama et al., "Clinical significance of the folate receptor beta expression in rheumatoid synovial macrophages", Rheumatoid, Japan College of Rheumatology, 41(2): 265, 2001.
Matsuyama et al., "Activation and pathological significance of macrophages in rheumatoid synovitis", Clinical Immunity, Japan, Kagaku Hyoronsha, Tokyo, 30(2): 214-219, 1998.
Mestas et al. "Of Mice and Not Men: Differences between Mouse and Human Immunology", J. of Immunology, 172, pp. 2731-2738, 2004.
Mukasa et al., "Function analysis of folate receptor-β in a RA synovial membrane macrophage cell line", Rheumatoid, Japan College of Rheumatology, 40(2): 378, 2000.
Mulherin et al., "Synovial tissue macrophage populations and articular damage in rheumatoid arthritis", Arthritis and Rheumatism, vol. 39, No. 1, pp. 115-124, 1996.
Murakami et al., "18F-Labelled Annexin V: A PET Tracer for Apoptosis Imaging", European Journal of Nuclear Medicine and Molecular Imaging, vol. 31, No. 4, pp. 469-474, Apr. 2004.
Nagayoshi et al., "Effectiveness of Anti-Folate Receptor β Antibody Conjugated with Truncated *Pseudomonas* Exotoxin in the Targeting of Rheumatoid Arthritis Synovial Macrophages", Arthritis and Rheumatism, vol. 52, pp. 2666-2675, Sep. 2005.
Nair et al., "Folate Analogues Altered in the C9-N10 Bridge Region. 10-Oxafolic Acid and 10-Oxaaminopterin", Journal of Medicinal Chemistry, vol. 19, No. 6, pp. 825-829, 1976.
Nair et al., "Folate Analogues Altered in the C9-N10 Bridge Region: N10-Tosylisohomofolic Acid and N10-Tosylisohomoaminopterin", Journal of Medicinal Chemistry, vol. 21, No. 7, pp. 673-677, 1978.
Nair et al., "Folate Analogues Altered in the C9-N10 Bridge Region: 11-Thiohomofolic Acid", Journal of Medicinal Chemistry, vol. 22, No. 7, pp. 850-855, 1979.
Nair et al., "Folate Analogues Altered in the C9-N10 Bridge Region. 14. 11-Oxahomofolic Acid, a Potential Antitumor Agent", Journal of Medicinal Chemistry, vol. 23, pp. 59-65, 1980.
Nair et al., "Folate Analogues Altered in the C9-N10 Bridge Region. 18. Synthesis and Antitumor Evaluation of 11-Oxahomoaminopterin and Related Compounds", Journal of Medicinal Chemistry, vol. 24, pp. 1068-1073, 1981.
Nair et al., "Folate Analogues. 20. Synthesis and Antifolate Activity of 1, 2, 3, 4, 5, 6,-Hexahydrohomofolic Acid", Journal of Medicinal Chemistry, vol. 26, pp. 135-140, 1983.
Nair et al., "Folate Analogues. 21. Synthesis and Antifolate and Antitumor Activities of N10-(Cyanomethyl)-5,8-dideazafolic Acid", Journal of Medicianal Chemistry, vol. 26, pp. 605-607, 1983.
Nair et al., "Folate Analogues. 22. Synthesis and Biological Evaluation of Two Analogues of Dihydrofolic Acid Processing a 7,8-Dihydro-8-oxapterin Ring System", Journal of Medicinal Chemistry, vol. 26, 1164-1168, 1983.
Nakashima-Matsushita et al, "Selective expression of folate receptor beta and its possible role in methotrexate transport in synovial macrophages from patients with rheumatoid arthritis", Arthritis Rheum. 42(8): 1609-1616, 1999.
Nehzat et al. "Four ovarian cancers diagnosed during laproscopic management of 1011 women with adnexal masses", Am J Obstet Gynecol., vol. 167, No. 3, pp. 790-796, Sep. 1992.
Oatis et al., "Synthesis of Quinazoline Analogues of Folic Acid Modified at Position 10", Journal of Medicinal Chemistry, vol. 20, No. 11, pp. 1393-1396, 1977.
Olma et al., "4-[18F]fluorophenyl ureas via carbamate-4-nitrophenyl esters and 4-[18F]Fluoroaniline", Journal of Labeled Compd. and Radiopnarm, vol. 49, pp. 1037-1050, 2006.
Paigen et al., "Variation in susceptibility to atherosclerosis among inbred strains of mice", Atherosclerosis, vol. 57, No. 1, pp. 65-73, 1985.
Pasterkamp et al. "Techniques characterizing the coronary atherosclerotic plaque: Influence on clinical decision making?", J. Amer. Coll. Cardiol. 36:13-21, 2000.
Paulos et al. "Folate Receptor-Mediated Targeting of Therapeutic and Imaging Agents to Activated Macrophages in Rheumatoid Arthritis", Advanced Drug Delivery Reviews, vol. 56, No. 8, pp. 1205-1217, 2004.
Pelegrin et al., "Antibody-Fluorescein Conjugates for Photoimmunodiagnosis of Human Colon Carcinoma in Nude Mice", Institute of Biochemistry, University of Lausanne, vol. 67, No. 10, pp. 2529-2537, 1991.
Plante et al., "Polyglutamyl and Polylysyl Derivatives of the Lysine Analogues of Folic Acid and Homofolic Acid", Journal of Medicinal Chemistry, vol. 19, No. 11, pp. 1295-1299, 1976.
U.S. Appl. No. 14/187,844, Low et al.
Rampone et al., "Ovarian cancer screening by transvaginal color Doppler ultrasonography", Minerva Ginecologica, vol. 53, Suppl. 1 al N 1, pp. 125-128, 2001.
Reddy et al., "Optimization of Folate-Conjugated Liposomal Vectors for Folate Receptor-Mediated Gene Therapy", J. Pharm. Sciences 88: 1112-1118, 1999.
Reddy et al., "Folate-Mediated Targeting of Therapeutic and Imaging Agents to Cancers", Critical Reviews in Ther. Drug Carrier Systems 15: 587-627, 1998.
Reddy et al., "Folate receptor specific anti-tumor activity of folate-mitomycin conjugates", Cancer Chemother. Pharmacol., 58(2): 229-36, 2006.
Reles et al., "Transvaginal Color Doppler Sonography and Conventional Sonography in the Preoperative Assessment of Adnexal Masses", Journal of Clinical Ultrasound, vol. 25, No. 5, pp. 217-225, Jun. 1997.
Roberts, et al., "Folic Acid Analogs. Modifications in the Benzene-Ring Region. 3. Neohomofolic and Neobishomofolic Acids. An Improved Synthesis of Folic Acid and Its Analogs". Journal of Medicinal Chemistry, 16(6): 697-699, 1973.

(56) References Cited

OTHER PUBLICATIONS

Roberts et al., "Folic Acid Analogs. Modifications in the Benzene-Ring Region. 2. Thiazole Analogs", Journal of Medicinal Chemistry, 15 (12): 1310-1312, 1972.
Roberts et al., "Folic Acid Analogs. Modifications in the Benzene-Ring Region. 1. 2'- and 3'-Azafolic Acids", Journal of Medicinal Chemistry, 14(2): 125-130, 1971.
Roberts et al., "Folic Acid Analogs. Modifications in the Benzene-Ring Region. 4. 3'- Ethyl- and 3'-Isopropylfolic Acids", Journal of Medicinal Chemistry, vol. 17, No. 2, pp. 219-222, 1974.
Rouzi et al., "Lapascopic Ovarian Cystectomy: Selection of Patients and Consequences of Rupture of Ovarian Malignancy", Annals of Saudi Medicine, vol. 17, No. 3, pp. 321-325, 1997.
Rudd et al., "Imaging Atherosclerotic Plaque Inflammation with [<18>F]-Fluorodeoxyglucose Positron Emission Tomography", Circulation, vol. 105, No. 23, pp. 2709-2710, 2002.
Sato et al., "Usefulness of Mass Screening for Ovarian Carcinoma Using Transvaginal Ultasonography", American Cancer Society, vol. 89, No. 3, pp. 582-588, Aug. 2000.
Sevick-Muraca et al., "Fluorescence and Absorption Contrast Mechanisms for Biomedical Optical Imaging Using Frequency-Domain Techniques", Photochemistry and Photobiology, vol. 66, No. 1, pp. 55-64, 1997.
Sheski et al., "Endoscopic Treatment of Early-Stage Lung Cancer", Division of Pulmonary, Allergy, Care, and Occupational Medicine at IU School of Medicine, vol. 7, No. 1, pp. 35-44, Jan./Feb. 2000.
Shoup et al., "Synthesis of Fluorine-18-Labeled Biotin Derivatives: Biodistribution and Infection Localization", J. Nuclear Medicine, vol. 35, No. 10, pp. 1685-1690, 1994.
Sijtsema et al., "Confocal Direct Imaging Raman Microscope: Design and Application in Biology", Applied Spectroscopy, vol. 52, Issue 3, pp. 348-355, 1998.
Sima et al., "Experimental obstructive coronary atherosclerosis in the hyperlipidemic hamster", J Submicrosc Cytol Pathol, vol. 22, No. 1, pp. 1-16, 1990.
Simionescu et al., "Prelesional modifications of the vessel wall in hyperlipidemic atherogenesis: Extracellular accumulation of modified and reassembled lipoproteins", Ann. NY Acad. Sci., 1990, vol. 598, pp. 1-16.
Smart et al., "Protein kinase C activators inhibit receptor-mediated potocytosis by preventing internalization of caveolae", Journal of Cell Biology, vol. 124, No. 3, pp. 307-313, 1994.
Solomin et al., "Computerized Tomography in Ovarian Cancer", Gynecologic Oncology, vol. 15 pp. 48-55, 1983.
Sudimack et al., "Targeted drug delivery via the folate receptor", Advanced Drug Delivery Reviews, vol. 41, pp. 147-162, 2000.
Sun et al., "Anhydrous Tetrabutylammonium Fluoride", J. Am. Chem. Soc., vol. 127, No. 7, pp. 2050-2051, 2005.
Sun et al., "Room-Temperature Nucleophilic Aromatic Fluorination: Experimental and Theoretical Studies", Angew. Chem. Int. Ed., No. 45, pp. 2720-2725, 2006.
Sundstrum et al., "Establishment and characterization of a human histiocytic lymphoma cell line (U-937)", International Journal of Cancer, vol. 17, No. 5, pp. 565-577, 1976.
Sutcliffe-Goulden, "Solid Phase Synthesis of [18F]Labelled Peptides for Positron Emission Tomography", Bio. & Medicin. Chem. Letters, No. 10, pp. 1501-1503, 2000.
Tan et al., "A Complete Remote-Control System for Reliable Preparation of [18F]altanserin", Applied Radiation and Isotopes, vol. 50, pp. 923-927, 1999.
Temple, Jr. et al., "Synthesis of Pseudo Cofactor Analogues as Potential Inhibitors of the Folate Enzymes", Journal of Medicinal Chemistry, vol. 25, pp. 161-166, 1982.
Toffoli et al., "Expression of Folate Binding Protein as a Prognostic Factor for Response to Platinum-Containing Chemotherapy and Survival in Human Ovarian Cancer", Int. J. Cancer, vol. 79, pp. 121-126, 1998.
Toffoli et al., "Overexpression of Folate Binding Protein in Ovarian Cancers", Int. J. Cancer (Pred. Oncol.), vol. 74., pp. 193-198, 1997.

Turk et al., "Folate-targeted imaging of activated macrophage in rats with adjuvant-induced arthritis", Arthritis and Rheumatism, vol. 46, No. 7, pp. 1947-1955, 2002.
Urban, "Screening for ovarian cancer: We now need a definitive randomized trial", BMJ, vol. 319, pp. 1317-1318, Nov. 1999.
Van Noort et al., "Cell Biology of Autoimmune Diseases", International Review of Cytology, vol. 178, pp. 127-204, 1998.
Vo-Dinh et al., "In Vivo Cancer Diagnosis of the Esophagus Using Differential Normalized Fluorescence (DNF) Indices", Lasers in Surgery and Medicine, vol. 16, pp. 41-47, 1995.
Wang et al., "Chemokines and their role in cardiovascular diseases", TCM, vol. 8, pp. 169-174, 1998.
Wang et al. "Synthesis, Purification, and Tumor Cell Uptake of Ga-Deferoxamine-Folate, a Potential Radiopharmaceutical for Tumor Imaging", American Chemical Society, Bioconjugate Chem., 1996, 7(1): 56-62, 1996.
Weinstock et al., "Folic Acid Analogs. II. p-{[2,6-Diamino-8-purinyl)methyl]amino}-benzoyl-L-glutamic Acid and Related Compounds", Journal of Medicinal Chemistry, 1970, 13(5): 995-997, 1970.
Weissleder et al., "In vivo imaging of tumors with protease-activated near-infrared fluorescent probes", Nature Biotechnology, vol. 17, pp. 375-378, Apr. 1999.
Weitman et al., "The folate receptor in central nervous system malignancies of childhood", Journal of Neuro-Oncology, vol. 21, pp. 107-112, 1994.
Westerhof et al., Carrier-and Receptor-Mediated Transport of Folate Antagonists Targeting Folate-Dependent Enzymes: Correlates of Molecular-Structure and Biological Activity, Molecular Pharmacology, 1995, 48: 459-471, 1995.
Whitehurst et al., "Development of an alternative light source to lasers for biomedical applications", SPIE, vol. 2629, pp. 291-298, 1993.
Wu et al., "Expression of Folate Receptor Type a in Relation to Cell Type Malignancy, and Differentiation in Ovary, Uterus and Cervix", Cancer Epidemiology, Biomarkers & Prevention, vol. 8, pp. 775-782, 1999.
Yavorsky et al., "Antiparticles", Handbook on Physics, pp. 339-340, 1984.
Zeisel et al., "Choline, an Essential Nutrient for Humans", The Faseb Journal, vol. 5, No. 7, pp. 2093-2098, 1991.
Delaloye et al., "Tumor imaging with monoclonal antibodies", Seminars in Nuclear Medicine, 25:144-164, 1995.
Reubi, "The role of peptides and their receptors as tumor markers", Endocrinology & Metabolism Clinics of North America, 22: 917-939, 1993.
Garin-Chesa et al., "Trophoblast and ovarian cancer antigen LK26. Sensitivity and specificity in immunopathology and molecular identification as a folate-binding protein", American Journal of Pathology, 142: 557-567, 1993.
Patrick et al., "Folate receptors as potential therapeutic targets in choroid plexus tumors of SV40 transgenic mice", Journal of Neuro-Oncology, 32: 111-123, 1997.
Weitman et al., "Distribution of the folate receptor GP38 in normal and malignant cell lines and tissues", Cancer Research, 52: 3396-3401, 1992.
Mathias et al., "Indium-111-DTPA-folate as a potential folate-receptor-targeted radiopharmaceutical", Journal of Nuclear Medicine, 39: 1579-1585, 1998.
Acosta et al., "Chromoendoscopy—where is it useful?", Journal of Clinical Gastroenterology, 27:13-20,1998.
Fleischer, "Chromoendoscopy and magnification endoscopy in the colon", Gastrointestinal Endoscopy, 49: S45-49, 1999.
Stepp et al., "Fluorescence endoscopy of gastrointestinal diseases: basic principles, techniques, and clinical experience", Endoscopy, 30: 379-386, 1998.
Ballou et al., "Tumor detection and visualization using cyanine fluorochrome-labeled antibodies", Biotechnology Progress, 13: 649-658, 1997.
Licha et al., "Synthesis, characterization, and biological properties of cyanine-labeled somatostatin analogues as receptor-targeted fluorescent probes", Bioconjugate Chemistry, 12: 44-50, 2001.

(56) References Cited

OTHER PUBLICATIONS

Becker et al., "Receptor-targeted optical imaging of tumors with near-infrared fluorescent ligands", Nature Biotechnology, 19: 327-331, 2001.
Terpetschnig et al., "Synthesis of squaraine-N-hydroxysuccinimide esters and their biological application as long-wavelength fluorescent labels", Analytical Biochemistry, 217: 197-204, 1994.
Mujumdar et al., "Cyanine dye labeling reagents containing isothiocyanate groups", Cytometry, 10: 11-19, 1989.
Wang et al., "Design and synthesis of [111In]DTPA-folate for use as a tumor-targeted radiopharmaceutical", Bioconjugate Chemistry, 8: 673-679, 1997.
Dimartino et al., "Antiarthritic and immunoregulatory activity of spirogermanium", Journal of Pharmacology an Experimental Therapeutics, 236: 103-110, 1986.
Ross et al., "Differential regulation of folate receptor isoforms in normal and malignant tissues in vivo and in established cell lines. Physiologic and clinical implications", Cancer, 73: 2432-2443, 1994.
Ross et al., "Folate receptor type beta is a neutrophilic lineage marker and is differentially expressed in myeloid leukemia", Cancer, 85: 348-357, 1999.
Curtin et al., "Stage IV ovarian cancer: impact of surgical debulking", Gynecologic Oncology, 64: 9-12, 1997.
Munkarah et al., "Prognostic significance of residual disease in patients with stage IV epithelial ovarian cancer", Gynecologic Oncology, 64: 13-17, 1997.
Murolo et al., "Ultrasound examination in ovarian cancer patients. A comparison with second look laparotomy", Journal of Ultrasound in Medicine, 8: 441-443, 1989.
Piver et al., "Second-look laparoscopy prior to proposed second-look parotomy", Obstetrics and Gynecology, 55: 571, 1980.
Bell et al., "Intraoperative radioimmunodetection of ovarian cancer using monoclonal antibody B72.3 and a portable gamma-detecting probe", Obstetrics and Gynecology, 76: 607-677, 1990.
Reuter et al., "Detection of colorectal carcinomas by intraoperative RIS in addition to preoperative RIS: surgical and immunohistochemical findings", European Journal of Nuclear Medicine, 19: 102-109, 1992.
Hornung et al., "Minimally-invasive debulking of ovarian cancer in the rat pelvis by means of photodynamic therapy using the pegylated photosensitizer PEG-m-THPC", British Journal of Cancer, 81: 631-637, 1999.
Folli et al., "Immunophotodiagnosis of colon carcinomas in patients injected with fluoresceinated chimeric antibodies against carcinoembryonic antigen", Proceedings of the National Academy of Sciences of the United States of America, 89: 7973-7977, 1992.
Folli et al., "Antibody-indocyanin conjugates for immunophotodetection of human squamous cell carcinoma in nude mice", Cancer Research, 54: 2643-2649, 1994.
Bannwarth et al., "Methotrexate in rheumatoid arthritis. An update", Drugs, 47: 25-50, 1994.
Bettegowda, et al., Proc. Natl. Acad. ScL U.S.A., 102: 1145-1150, 2005.
Bunce, et al., Infect. Immun., 60: 2636-2640, 1992.
Claassen E. et al., "Preparation and characteristics of dichloromethylene diphosphonate-containing liposomes," J. Microencapsul., 3: 109-14, 1986.
Marceau et al., Bioorganics and Medical Chemistry Letters, 15(24): 5442-5445, 2005.
Novabiochem® Letters, "Resins for the synthesis of biotinylated and fluorescently-labeled peptides," 01/04, pp. 1-4, 2004.
Novabiochem® Letters, "Products for peptide ligation," 02/04, pp. 1-4, 2004.
Novabiochem® Letters, "Amino acids for Fmoc SPPS," 03/04, pp. 1-4, 2004.
Novabiochem® Letters, "PEG reagents," 04/04, pp. 1-4, 2004.
Leamon et al., "Folate-Liposome-Mediated Antisense Oligodeoxynucleotide Targeting to Cancer Cells: Evaluation in Vitro and in Vivo", Bioconjugate Chem., 14, 738-747, 2003.

Leamon et al., "Folate-mediated Drug Delivery: Effect of Alternative conjugate Chemistry", Journal of Drug Targeting, col. 7, No. 3, 157-169, 1999.
Marecos et al., "Antibody-Mediated versus Nontargeted Delivery in a Human Small Cell Lung Carcinoma Model", Bioconjugate Chemistry, 9:184-191 (1998).
"Osteomyelitis", XP-002569963, URL:http://emedicine.medscape.com/article/785020-overview>, retrieved Feb. 22, 2010.
Kennedy MD, "Folate-targeted imaging agents," Thesis submitted to the faculty of Purdue University in partial fulfillment of the requirements for the degree of Doctor of Philosophy, published Nov. 2004.
Holladay et al., "Riboflavin-mediated delivery of a macromolecule into cultured human cells," *Biochim Biophys Acta* 1426(1): 195-204 (1999).
Low PS, Leamon CP, Reddy JA, Green MA, Mathias C, Turk MJ, Waters DJ, Lu J, Lee RJ, Kennedy MD, "Folate-mediated delivery of therapeutic and imaging agents to cancer tissue," Gene, Drug Therapy, and Molecular Biology (Abstract), 2000.
Low, P.S., Leamon, C.P., Reddy, J.A., Green, M.A., Mathias, C., Turk, M.J., Waters, D.J., Lu, J., Lee, R.J. and Kennedy, M., "Folate-Mediated Delivery of Therapeutic and Imaging Agents to Cancer Tissues In Vivo," International Symposium on Tumor Targeted Delivery Systems, Bethesda, Maryland. British Journal of Pharmacology, vol. 134 (Abstract), 2001.
Kern, et al., "Evaluation of the Culprit Plaque and the Physiological Significance of Coronary Atherosclerotic Narrowings," Circulation, 2001; 103:3142-3149.
Phelps et al., Journal of Nuclear Medicine, 1975, 16(3): 210-224.
Snook et al., Br. J. Cancer, 1990, 62 (Suppl. X): 89-91.
Patton, Radiographics, 1998, 18: 995-1007.
Kanagaki et al., "Pituitary Gland and Parasellar Region," in *Magnetic Resonance Tomography*, Reiser et al. (eds.), 2008, p. 422.
Barnes, H. H., et al., "Purification of Catechol Siderophores by Boronate Affinity Chromatography: Identification of Chrysobactin From *Erwinia carotovora* subsp. *carotovora*", 1999, *BioMetals*, vol. 12, pp. 83-87.
Collins, Peter, et al., "Monosaccharides, Their Chemistry and Their Roles in Natural Products", 1995 *Wiley Publishers*, Book Reference.
Georgakoudi, Irene, et al., "In Vivo Flow Cytometry: A New Method for Enumerating Circulating Cancer Cells", Aug. 1, 2004, *Cancer Research*, No. 64, pp. 5044-5047.
Hanessian, Stephen, "Preparative Carbohydrate Chemistry", 1997 *Marcel Dekker, Inc.*, Book Reference.
Idanpaan-Heikkila, Ilona, et al., "Oligosaccharides Interfere With the Establishment and Progression of Experimental Pneumococcal Pneumonia", 1997, *The Journal of Infectious Diseases*, No. 176, pp. 704-712.
Iijima, Masatomi, et al., "IC202A, a New Siderophore With Immunosuppressive Activity Produced by *Streptoalloteichus* sp. 1454-19. I. Taxonomy, fermentation, isolation and biological activity.", Jan. 1999, *The Journal of Antibiotics* (Tokyo), vol. 52, No. 1, pp. 20-24.
Lingwood, Clifford A., "Oligosaccharide Receptors for Bacteria: A View to a Kill", 1998, *Curr Opin Chem Biol.*, pp. 695-700.
Michelson, Alan D., et al., "Evaluation of Platelet Function by Flow Cytometry", 2000, *Methods*, vol. 21, pp. 259-270.
Novak, J., et al., "In Vivo Flow Cytometer for Real-Time Detection and Quantification of Circulating Cells", Jan. 1, 2004 *Optics Letters*, vol. 29, No. 1, pp. 77-79.
Ratledge, Cohn, et al., "The Occurrence of Carboxymycobactin, the Siderophore of Pathogenic Mycobacteria, as a Second Extracellular Siderophore in *Mycobacterium smegmatis*", 1996 *Microbiology*, vol. 142, pp. 2207-2212.
Scharfman, Andree, et al., "Pseudomonas Aeruginosa Binds to Neoglycoconjugates Bearing Mucin Carbohydrate Determinants and Predominantly to sialyl-Lewis x Conjugates", 1999, *Glycobiology*, vol. 9, No. 8, pp. 757-764.
Schalk, Isabelle J., et al., "Iron-Free Pyoverdin Binds to Its Outer Membrane Receptor FpvA in Pseudomonas Aeruginosa: A New Mechanism for Membrane Iron Transport", 2001, *Molecular Microbiology*, vol. 39, No. 2, pp. 351-360.

(56) References Cited

OTHER PUBLICATIONS

Albrecht-Gary et al., "Bacterial Iron Transport: Coordination Properties of Pyoverdin PaA, a Peptidic Siderophore of Pseudomonas aeruginosa", 1994. *Inorg. Chem.*, 33 (26), pp. 6391-6402.
Henne, Walter A., et al., "Synthesis and Activity of a Folate Peptide Camptothecin Prodrug", (Aug. 9, 2006), *Bioorganic & Medicinal Chemistry Letters*, vol. 16, pp: 5350-5355.
Tang, Hailun, et al., "Prostate Targeting Ligands Based on N-Acetylated α-Linked Acidic Dipeptidase", (2003), *Biochemical and Biophysical Research Communications*, vol. 307, pp. 8-14.
Wosikowski, Katja, et al., "In Vitro and in Vivo Antitumor Activity of Methotrexate Conjugated to Human Serum Albumin in Human Cancer Cells", (May 2003), *Clinical Cancer Research*, vol. 9, pp. 1917-1926.
International Search Report and Written Opinion for PCT/US2007/023176 completed Aug. 4, 2008 (Aug. 4, 2008).
Wiener et al., "Targeting Dendrimer-Chelates to Tumors and Tumor Cells Expressing the High-Affinity Folate Receptor," *Investigative Radiology*, 1997; 32(12):748-754.
Paulos et al., "Ligand Binding and Kinetics of Folate Receptor Recycling in Vivo: Impact on Receptor-Mediated Drug Delivery," *Molecular Pharmacology*, 2004; 66:1406-1414.
He et al., "In vivo quantitation of rare circulating tumor cells by multiphoton intravital flow cytometry," Proc Nat Acad Sci USA, 2007; 104: 11760-11765.
Chen et al., "In vivo imaging of proteolytic activity in atherosclerosis," Circulation, 2002, 105: 2766-2771.
Mathias et al., "Synthesis of [99mTc]DTPA-Folate and Its Evaluation as a Folate-Receptor-Targeted Radiopharmaceutical", Bioconj. Chem., 2000; 11:253-257.
Linder et al., "In Vitro & In Vivo Studies with α-and y-Isomers of 99mTc-OXA-Folate Show Uptake of Both Isomers in Folate-Receptor (+) KB Cell Lines", Soc. Nucl. Med. Proc., May 2000; 41:5:119.
Ilgan et al., "99mTc-Ethylenedicysteine-Folate: A New Tumor Imaging Agent. Synthesis, labeling and Evaluation in Animals", Can. Biother. & Radiophar., 1998; 13:6:427-435.
Massoud et al., "Molecular imaging in living subjects: seeing fundamental biological processes in a new light", 2003, Genes Dev. 17: 545-580.
Caliceti et al., "Pharmacokinetic and biodistribution properties of poly9ethylene glycol)—protein conjugates", 2003, Adv. Drug Del. Rev. 55: 1261-1277.
Tamaki, et al., "PET in Oncology" Jpn J Cancer Clin, 2003, 49(6): 531-535.
Remington: The Science & Practice of Pharmacy, 21th Edition (Lippincott Williams & Wilkins, 2005).
Bendele et al., "Animal Models of Arthritis: Relevance to Human Disease", Toxicology Pathology, vol. 27, No. 1, pp. 134-142, 1999.
Tanaka, et al., "Digestive tract lesions and immunity," The Japanese Journal of Gastroenterology, 1994, vol. 91(2): 131-135.
Folate—FITC (http://www.medkoo.com/Anticancer-trials/EC-17.htm (downloaded on Aug. 8, 2013)).
Atherosclerosis (http://web.archive.org/web/20081207060136/http://en.wikipedia.org/wild/Atherosclerosis (archived on Dec. 7, 2008)).
Yang et al, Imaging Tumor Folate Receptors using radiolabeled folate and methotrexate, Jour Labelled Compounds and Radiopharmaceuticals, 1999, Sussex, GB, Vol Suppl 1, 42: S696-S697.
Ilgan et al., "Imaging tumor folate receptors using 111IN-DTPA-methotrexate." *Cancer Biother. Radiopharm.*, 1998, 13(3) pp. 177-184.
Akihiro H. et al., "Affinity for a-tocopherol transfer protein as a determinant of the biological activities of vitamin E analogs." *Federation of European Biochemical Societies*, 1997, vol. 409, pp. 105-108.
Kazuki S. et al., "Novel vitamin D3 antipsoriatic antedrugs: 16-En-22-oxa-1a,25-(OH)2D3 analogs," *Bioorganic & Medicinal Chemistry*, 2006, vol. 14, pp. 1838-1850.

Hisashi T. et al., "c-Fos protein as a target of anti-osteoclastogenic action of vitamin D, and synthesis of new analogs," journal article, *The Journal of Clinical Investigation*, 2006, vol. 116, No. 2, February, pp. 528-535.
Masato S. et al., "Synthesis and biological activities of new 1a,25-dihydroxy-19-norvitamin D3 analogs with modifications in both the A-ring and the side chain," journal article, *Bioorganic & Medicinal Chemistry*, 2006, 14(12) pp. 4277-4294.
Agoston E.S. et al., "Vitamin D Analogs as Anti-Carcinogenic Agents" *Anti-Cancer Agents in Medicinal Chemistry* 2006, 6(1), pp. 53-71.
Lonsdale, D., "A Review of the Biochemistry, Metabolism and Clinical Benefits of Thiamin(e) and Its Derivatives." *Evidence-Based Complementary & Alternative Medicine: eCAM.* Advance Access Publication, vol. 3, Feb. 2006, pp. 49-59.
Nosaka, K. et al., "Separate Determination of Anticoccidial Thiamine Analogs by High-Performance Liquid Chromatography." *ActaA Vitaminol. Et Enzymol.*, 1984, vol. 6 92), pp. 137-142.
Kandiko, C.T. et al., "Inhibition of Rat Brain Pyruvate Dehydrogenase by Thiamine Analogs." *Biochem. Pharmacology*, vol. 37, No. 22, (1988) pp. 4375-4380.
Spry, C. et al., "A Class of Pantothenic Acid Analogs Inhibits Plasmodium Falciparum Pantothenate Kinase and Represses the Proliferation of Malaria Parasites." *Antimicrobial Agents and Chemotherapy*, Nov. 2005, pp. 4649-4657.
Sargent, D.R. et al., "Antimetabolites of Pantothenic Acid, Ureido- and Carbamoyl-Derivatives." *Texas Reports on Biology and Medicine*, 1975, vol. 33, No. 3, pp. 433-443.
Hanck, A.B. et al., "Dexpanthenol (Ro 01-4709) in the treatment of constipation." Abstract, Acta Vitaminol Enzymol, 1982, vol. 4 (1-2), pp. 87-97.
Kagechika, H. et al., "Synthetic Retinoids: Recent Developments Concerning Structure and Clinical Utility." *J. Med. Chem.*, Sep. 22, 2005, vol. 48, No. 19, pp. 5875-5883.
Shealy, Y.F. "Synthesis and Evaluation of Some New Retinoids for Cancer Chemoprevention." *Preventive Medicine*, 1989, vol. 18, pp. 624-645.
Landuer, W. et al., "The Interaction in Teratogenic Activity of the Two Niacin Analogs 3-acetylpyridine and 6-ammonicotinamide," *J Experimental Zoology*, 1962, vol. 151, pp. 253-258.
Renz, P. et al., "Synthesis of 4-Aza-5, 6-diethylbenzimidazole and Biosynthetic Preparation of 4- and 7-Aza-5, 6-dimethylbenzimidazolylcobamide," *Z. Naturforsch*, 1997, vol. 52C, pp. 5287-5291.
Ayers, W.A., "Effect of Vitamin B12 and Analogs on the Respiration of a Marine Bacterium." *Archives of Biochemistry and Biophysics*, 1962, vol. 96, pp. 210-215.
Toraya, T. et al., "Immobilized Derivatives of Vitamin B12 Coenzyme and Its Analogs." *Methods in Enzymology*, 1980, vol. 67, pp. 57-66.
Ueda, M. et al., "Effect of Vitamin B12 Derivatives on Urinary Excretion of Methylmalonic Acid in Liver Diseases." *Acta Med. Okayama*, 1970, vol. 24, pp. 365-372.
Toraya, T. et al., "The Synthesis of Several Immobilized Derivatives of Vitamin B12 Coenzyme and Their Use as Affinity Adsorbents for a Study of Interactions of Diol Dehydrase with the Coenzyme." *Journal of Biological Chemistry*, 1980, vol. 255, No. 8, Apr. 25, pp. 3520-3525.
Takahata, Y. et al., "Synthesis, Properties and Microbiological Activity of Hydrophobic Derivatives of Vitamin B12." *J. Nutr. Sci. Vitaminol.*, 1995, vol. 14, pp. 515-526.
Kamao, M. et al., "Determination of Plasma Vitamin K by High Performance Liquid Chromatography with Fluorescence Detection Using Vitamin K Analogs as Internal Standards." *J. of Chromatography B.*, 2005, vol. 816, pp. 41-48.
Nishikawa, Y. et al., "Growth Inhibition of Hepatoma Cells Induced by Vitamin K and Its Analogs." *Journal of Biological Chemistry*, 1995, vol. 270, No. 47, Nov. 24, pp. 28304-28310.
Mack, D.O. et al., "The Carboxylation Activity of Vitamin K Analogs with Substitutions at Position 2, 3, or 5." *Journal of Biological Chemistry*, 1979, vol. 254, Apr. 25, pp. 2656-2664.

(56) References Cited

OTHER PUBLICATIONS

Mock, D.M. et al., "Urinary Biotin Analogs Increase in Humans During Chronic Supplementation: the Analogs are Biotin Metabolites." *The American Physiological Society*, 1997, pp. 83-85.
International Search Report for PCT/US2002/13890 completed Oct. 28, 2002 (Oct. 28, 2002).
Vesely, D.L. et al., "Biotin Analogs Activate Guanylate Cyclase." *Molecular and Cellular Biochemistry*, 1984, vol. 60, pp. 109-114.
Lambooy, J.P., "Riboflavin Analogs Utilized for Metabolism by a Lactobacillus Casei Mutant." *Int. J. Biochem.*, 1984, vol. 16, No. 2, pp. 231-234.
Nielsen, P. et al., "Phosphates of Riboflavin and Riboflavin Analogs: a Reinvestigation by High-Performance Liquid Chromatography." *Analytical Biochemistry*, 1983, vol. 130, pp. 359-368.
Arya, P. et al., "Design and Synthesis of Analogs of Vitamin E: Antiproliferative Activity Against Human Breast Adenocarcinoma Cells." *Bioorganic & Medicinal Chemistry Letters*, 1998, vol. 8, No. 18, pp. 2433-2438.
Trachewsky, D. "Antihypertensive Effect of Riboflavin Analogs in Rats with Mineralocorticoid-Induced Hypertension." *Hypertension*, 1981, vol. 3, No. 1, Jan.-Feb., pp. 75-80.
Skinner, W.A. et al., "Structure-Activity Relations in the Vitamin E Series. II. Derivatives of alpha-Tocopherol Substituted at the 5-Methyl Group." *J Med. Chem.*, 1962, vol. 12, pp. 64-66.
Neuzil, J. et al., "Vitamin E. Analogs: A New Class of Multiple Action Agents with Anti-Neoplastic and Anti-Atherogenic Activity." *Apoptosis*, 2002, vol. 7, pp. 179-187.
Politis, I. et al., "The Effect of Various Vitamin E Derivatives on the Urokinase-Plasmogen Activator System of Ovine Macrophages and Neutrophils." *British Journal of Nutrition*, 2003, vol. 89, pp. 259-265.
Wang, X. et al., "Vitamin E Analogs Trigger Apoptosis in HER2/erbB2-Overexpressing Breast Cancer Cells by Signaling Via the Mitochondrial Pathway." *Biochemical and Biophysical Research Communication*, 2005, vol. 326, pp. 282-289.
Kilbourn et al, Fluorine-18 labeling of proteins, 1987, J Nucl Med, 28: 462-470.
Coussens et al, Inflammation and cancer, 2002, Nature, 420: 860-867.
PCT International Search Report and Written Opinion for PCT Application No. PCT/US2010/026406, mailed Apr. 15, 2010.
Jallad et al, Dissertation Abstracts International, 2001, 65(5B), p. 2390.
Stummer et al, J Neurosurg, 2000, 93:1003-1013.
Kennedy et al, Dissertation Abstracts International, 2001, 65(5B), p. 2354.
Nisshoshi, 1994, The Japanese Journal of Gastoenterology, 91(2): 131-135.
Extended European Search Report for EP 02734139, completed Jun. 11, 2004.
International PCT Search Report and Written Opinon for PCT Application No. PCT/US2008/053293, completed Mar. 10, 2009.
International PCT Search Report and Written Opinon for PCT Application No. PCT/US2005/046708, completed Sep. 20, 2006.
Extended European Search Report for EP 05855293, completed Jun. 12, 2009.
Extended European Search Report for EP 04753487, completed Jun. 16, 2006.
International PCT Search Report and Written Opinon for PCT Application No. PCT/US2004/016667, completed Sep. 22, 2004.
International PCT Search Report and Written Opinon for PCT Application No. PCT/US2008/064711, completed May 19, 2010.
International PCT Search Report and Written Opinon for PCT Application No. PCT/US2006/037112, completed Nov. 14, 2007.
Reddy J A et al: "Expression and functional characterization of the beta-isoform of the folate receptor on CD34(+) cells," Blood, vol. 93, No. 11, Jun. 1, 1999 (Jun. 1, 1999), pp. 3940-3948, XP002300805.
Japanese Translation of PCT International Application No. 2005-519078.
Japanese Translation of PCT International Application No. 2004-530678.
Extended European Search Report for EP 07867348, completed Jul. 29, 2010.
FDA Drug Label for "Cis-MDP™," Oct. 19, 2004, 9 pages.
FDA Drug Label for "MDP-25," Jul. 8, 2009, 21 pages.
Yang et al., Clin. Cancer Res., vol. 13, pp. 2557-2567 (2007).
Turk, M. et al., "Folate-conjugated liposomes preferentially target macrophages associated with ovarian carcinoma," Cancer Letters, 213, pp. 165-172 (2004).
Kalgutkar et al, "Ester and Amide derivatives of the nonsteroidal anti-inflammatory drug, Indomethacin, as selective cyclooxygenase-2 inhibitors," J. Med. Chem., 2000, 43, pp. 2860-2870.
Leamon et al, "Cytoxicity of Momordin-Folate conjugates in cultured human cell" J. Biol Chem, 267: 35: pp. 24966-24971, 1992.
The Merck Manuals Online Medical Library, (online), Whitehouse Station, NJ: Merck Research Laboratories, 2010-2013, retrieved on May 26, 2014 from http://www.merckmanuals.com/professional/musculoskeletal_and_connective_tissue_disorders/joint_disorders/osteoarthritis_oa.html?qt=osteoarthristis&alt=sh. Osteoarthritis.

* cited by examiner

METHOD OF IMAGING OSTEOARTHRITIS USING A FOLATE CONJUGATE

CROSS REFERENCE TO RELATED APPLICATIONS

This application is a continuation application of U.S. patent application Ser. No. 12/391,981, filed Feb. 24, 2009, which is a continuation application of U.S. patent application Ser. No. 11/481,264, filed Jul. 5, 2006, which claims priority under 35 U.S.C. §119(e) to U.S. Provisional Application Ser. No. 60/696,740, filed on Jul. 5, 2005, and to U.S. Provisional Application Ser. No. 60/801,636, filed on May 18, 2006, each application incorporated by reference herein in its entirety.

FIELD OF THE INVENTION

This invention relates to methods for treating and diagnosing disease states mediated by monocytes. More particularly, ligands that bind to monocytes are complexed with an imaging agent for use in diagnosis or to an immunogen, a cytotoxin, or an agent for altering monocyte function for use in the treatment of monocyte-mediated disease.

BACKGROUND

The mammalian immune system provides a means for the recognition and elimination of foreign pathogens. While the immune system normally provides a line of defense against foreign pathogens, there are many instances where the immune response itself is involved in the progression of disease. Exemplary of diseases caused or worsened by the host's own immune response are autoimmune diseases and other diseases in which the immune response contributes to pathogenesis. For example, macrophages are generally the first cells to encounter foreign pathogens, and accordingly, they play an important role in the immune response, but activated macrophages can also contribute to the pathophysiology of disease in some instances.

The folate receptor is a 38 KD GPI-anchored protein that binds the vitamin folic acid with high affinity (<1 nM). Following receptor binding, rapid endocytosis delivers the vitamin into the cell, where it is unloaded in an endosomal compartment at low pH. Importantly, covalent conjugation of small molecules, proteins, and even liposomes to folic acid does not block the vitamin's ability to bind the folate receptor, and therefore, folate-drug conjugates can readily be delivered to and can enter cells by receptor-mediated endocytosis.

Because most cells use an unrelated reduced folate carrier to acquire the necessary folic acid, expression of the folate receptor is restricted to a few cell types. With the exception of kidney, choroid plexus, and placenta, normal tissues express low or nondetectable levels of the folate receptor. However, many malignant tissues, including ovarian, breast, bronchial, and brain cancers express significantly elevated levels of the receptor. In fact, it is estimated that 95% of all ovarian carcinomas overexpress the folate receptor. It has been reported that the folate receptor β, the nonepithelial isoform of the folate receptor, is expressed on activated (but not resting) synovial macrophages. Thus, folate receptors are expressed on a subset of macrophages (i.e., activated macrophages).

SUMMARY

It is unknown, however, whether folate receptors are expressed on monocytes, the precursor cells for macrophages. Thus, Applicants have undertaken to determine whether folate receptors are expressed on monocytes and whether monocyte targeting, using a ligand such as folate, to deliver cytotoxic or other inhibitory compounds to monocytes, is useful therapeutically. Applicants have also undertaken to determine whether an imaging agent linked to a ligand capable of binding to monocytes may be useful for diagnosing inflammatory pathologies.

A method is provided for treating and diagnosing disease states mediated by monocytes. In one embodiment, the monocytes are activated monocytes. In one embodiment, disease states mediated by monocytes are treated by delivering an immunogen to the monocytes, by linking the immunogen to a ligand that binds to monocytes, to redirect host immune responses to monocytes. In another embodiment, monocytes can be inactivated or killed by other methods such as by the delivery to monocytes of cytotoxins or other compounds capable of altering monocyte function.

In the embodiment where an immunogen is delivered to monocytes to inactivate or kill monocytes, ligands that bind to monocytes are conjugated with an immunogen to redirect host immune responses to the monocytes, or the ligand is conjugated to a cytotoxin for killing of monocytes. Ligands that can be used in the conjugates of the present invention include those that bind to receptors expressed on monocytes (e.g., activated monocytes), such as the folate receptor, or ligands such as monoclonal antibodies directed to cell surface markers expressed on monocytes or other ligands that bind to activated monocytes. In another embodiment, ligands that bind to monocytes are conjugated to an imaging agent and the conjugate is used to diagnose diseases mediated by monocytes.

In another embodiment, a method is provided for diagnosing a disease state mediated by monocytes. The method comprises the steps of isolating monocytes from a patient suffering from a monocyte-mediated disease state, contacting the monocytes with a composition comprising a conjugate or complex of the general formula $$A_b\text{-}X$$

where the group $A_b$ comprises a ligand that binds to monocytes and the group X comprises an imaging agent, and quantifying the percentage of monocytes that expresses a receptor for the ligand. In another embodiment, $A_b$ comprises a folate receptor binding ligand. In yet another embodiment, $A_b$ comprises a monocyte-binding antibody or antibody fragment or other ligands that bind to activated monocytes. In another embodiment, the imaging agent comprises a metal chelating moiety that binds an element that is a radionuclide. In still another embodiment, the imaging agent comprises a chromophore selected from the group consisting of fluorescein, Oregon Green, rhodamine, phycoerythrin, Texas Red, and AlexaFluor 488.

In another embodiment, a method is provided for diagnosing a disease state mediated by monocytes. The method comprises the steps of administering parenterally to a patient a composition comprising a conjugate or complex of the general formula $$A_b\text{-}X$$

where the group $A_b$ comprises a ligand that binds to monocytes and the group X comprises an imaging agent, and quantifying the percentage of monocytes that expresses a receptor for the ligand.

In another embodiment, a method is provided for treating a disease state mediated by monocytes. The method comprises the steps of administering to a patient suffering from a monocyte-mediated disease state an effective amount of a composition comprising a conjugate or complex of the general formula A_b-X where the group $A_b$ comprises a ligand that binds to monocytes and the group X comprises an immunogen, a cytotoxin, or a compound capable of altering monocyte function, and eliminating the monocyte-mediated disease state.

In yet another embodiment, a compound for diagnosing or treating a disease state mediated by monocytes is provided. The compound is selected from the following group of compounds:

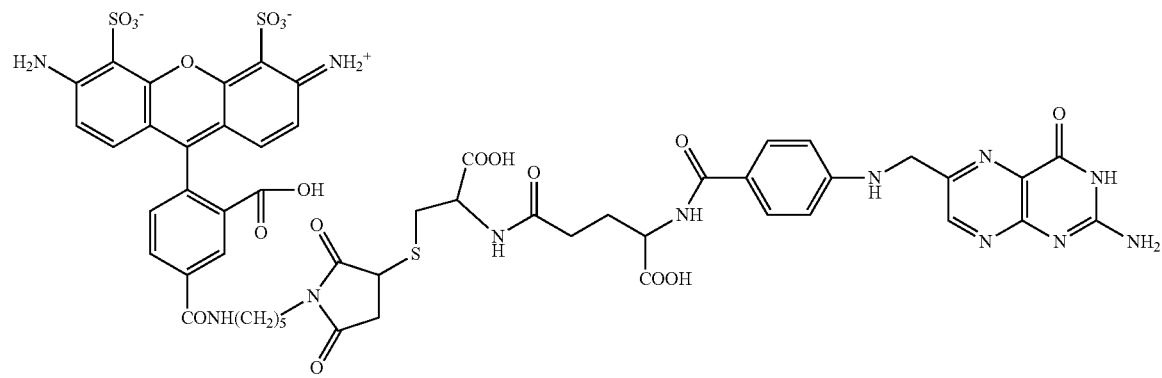

Alexa Fluor 488- Cys-γ-Glu-Pteroic Acid
MW 1242.21

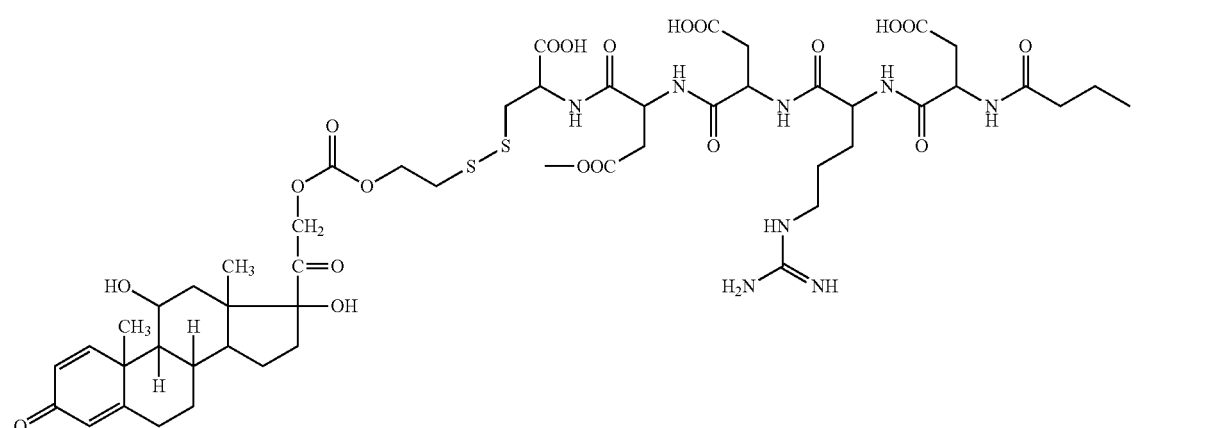

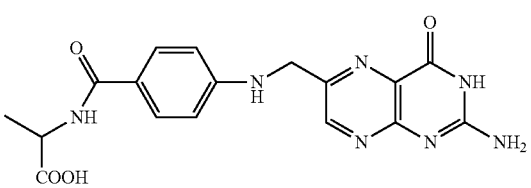

Prednisolone-Cys-Asp-Asp-Arg-Asp-γ-Glu-Pteroic Acid
MW 1507.5

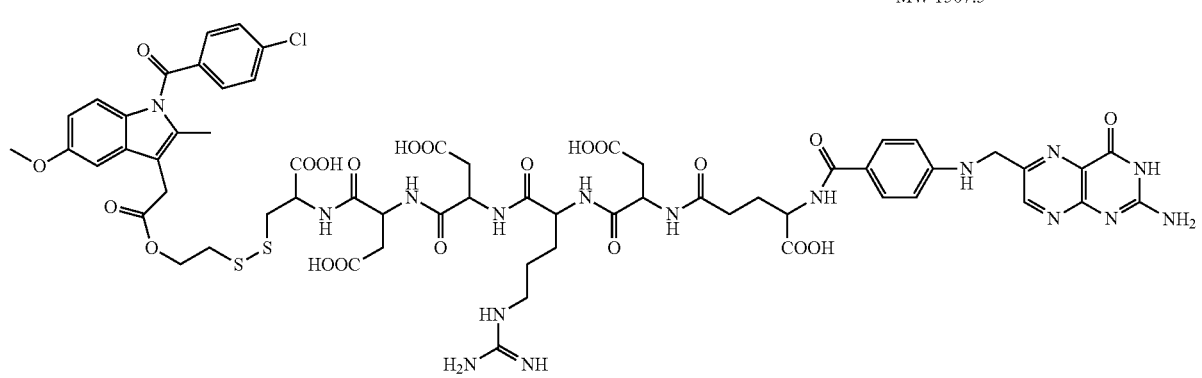

Indomethacin-Cys-Asp-Asp-Arg-Asp-γ-Glu-Pteroic Acid
MW 1462

-continued
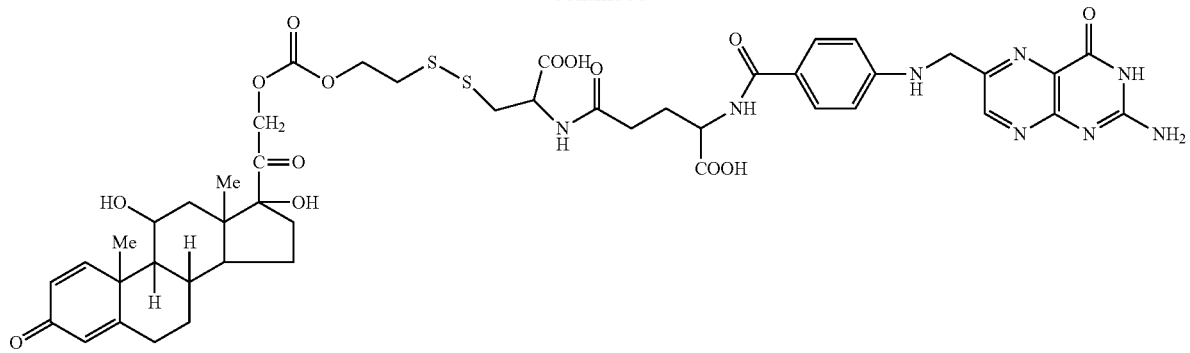
Prednisolone-Cys--g-Glu-Pteroic Acid
MW 1007.10
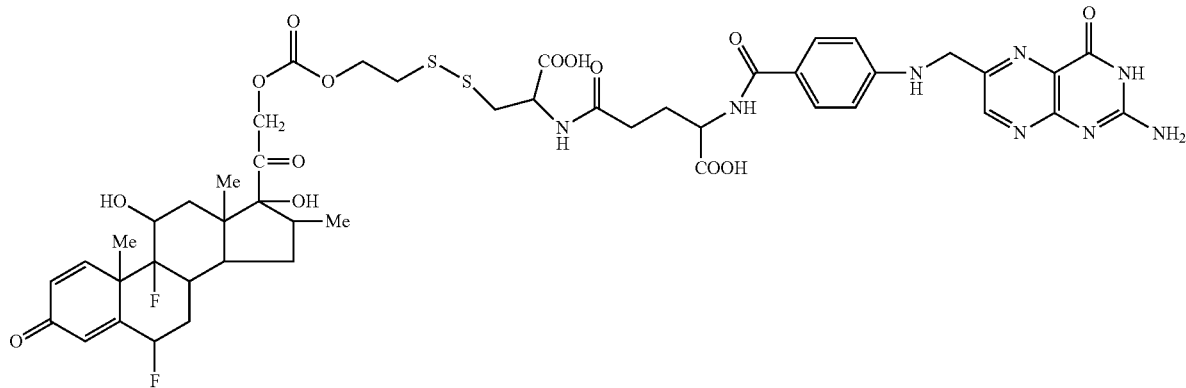
Diclofenac-Cys-Asp-Asp-Arg-Asp-γ-Glu-Pteroic Acid
MW 1386
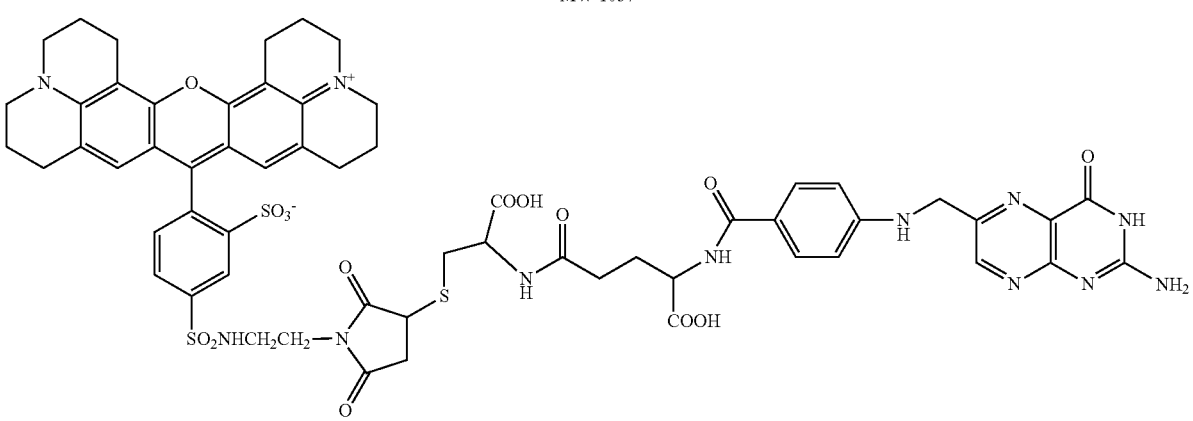
Folate-Cys-Flumethansone
MW 1057
Texas Red-Cys-γ-Glue-Pteroic Acid
MW 1273.37

-continued

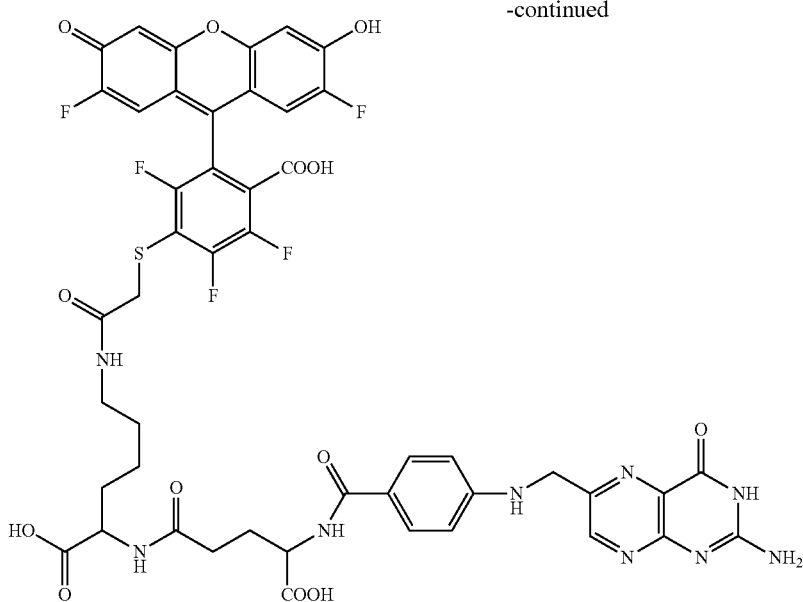

DETAILED DESCRIPTION

Figure 1:
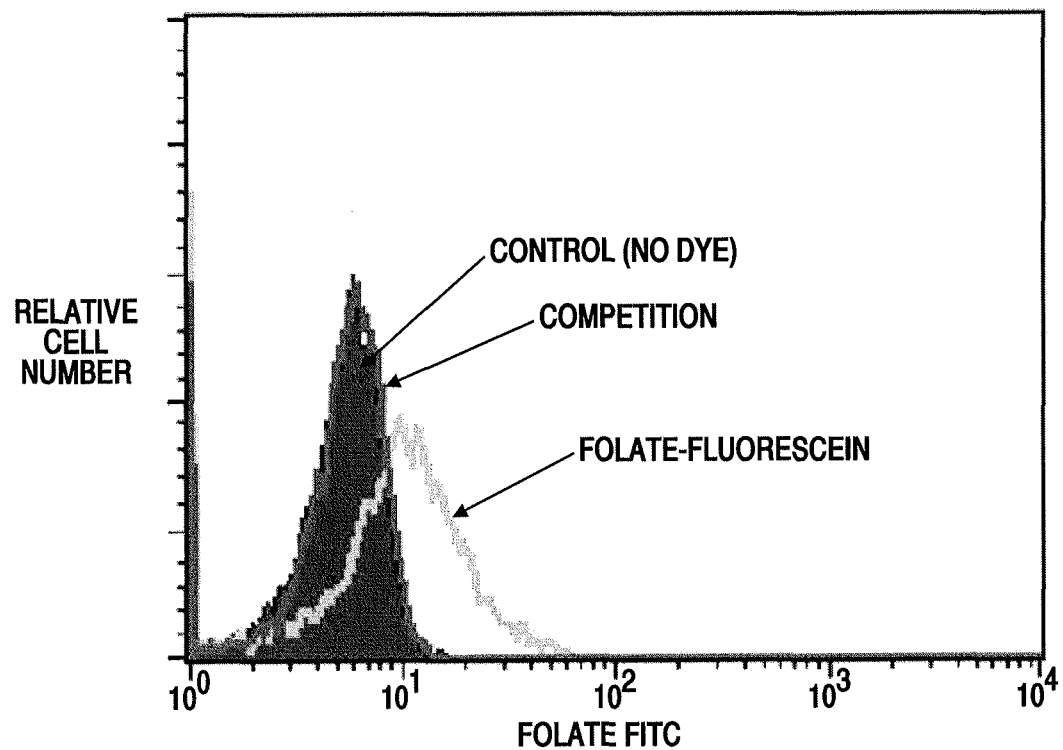
FIG. 1 shows folate-fluorescein binding to human monocytes isolated from peripheral blood and left untreated or preincubated with a 100-fold excess of unlabeled folic acid to compete with folate-fluorescein for binding.

Methods are provided for treating and diagnosing disease states mediated (e.g., caused or augmented) by monocytes. Exemplary disease states include fibromyalgia, rheumatoid arthritis, osteoarthritis, ulcerative colitis, Crohn's disease, psoriasis, osteomyelitis, multiple sclerosis, atherosclerosis, pulmonary fibrosis, sarcoidosis, systemic sclerosis, organ transplant rejection (GVHD), lupus erythematosus, Sjögren's syndrome, glomerulonephritis, inflammations of the skin (e.g., psoriasis), and chronic inflammations. Such disease states can be diagnosed by isolating monocytes (e.g., whole blood or peripheral blood monocytes) from a patient suffering from such disease state, contacting the monocytes with a composition comprising a conjugate of the general formula $A_b$-X wherein the group $A_b$ comprises a ligand that binds to monocytes, and the group X comprises an imaging agent, and quantifying the percentage of monocytes expressing a receptor for the ligand.

Such disease states can also be diagnosed by administering parenterally to a patient a composition comprising a conjugate or complex of the general formula $A_b$-X where the group $A_b$ comprises a ligand that binds to monocytes and the group X comprises an imaging agent, and quantifying the percentage of monocytes that expresses a receptor for the ligand.

Monocyte-mediated disease states can be treated in accordance with the methods disclosed herein by administering an effective amount of a composition $A_b$-X wherein $A_b$ comprises a ligand that binds to monocytes and wherein the group X comprises an immunogen, a cytotoxin, or a compound capable of altering monocyte function. Such monocyte targeting conjugates, when administered to a patient suffering from a monocyte-mediated disease state, work to concentrate and associate the conjugated cytotoxin, immunogen, or compound capable of altering monocyte function with the population of monocytes to kill the monocytes or alter monocyte function. The conjugate is typically administered parenterally, but can be delivered by any suitable method of administration (e.g., orally), as a composition comprising the conjugate and a pharmaceutically acceptable carrier therefor. Conjugate administration is typically continued until symptoms of the disease state are reduced or eliminated, or administration is continued after this time to prevent progression or reappearance of the disease.

As used herein, the terms "eliminated" and "eliminating" in reference to the disease state, mean reducing the symptoms or eliminating the symptoms of the disease state or preventing the progression or the reoccurrence of disease.

As used herein, the terms "elimination" and "deactivation" of the monocyte population that expresses the ligand receptor mean that this monocyte population is killed or is completely or partially inactivated which reduces the monocyte-mediated pathogenesis characteristic of the disease state being treated.

As used herein, "mediated by" in reference to diseases mediated by monocytes means caused by or augmented by. For example, monocytes can directly cause disease or monocytes can augment disease states such as by stimulating other immune cells to secrete factors that mediate disease states, such as by stimulating T-cells to secrete TNF-α. Illustratively, monocytes themselves may also harbor infections and cause disease and infected monocytes may cause other immune cells to secrete factors that cause disease such as TNF-α secretion by T-cells.

In one embodiment, monocyte-mediated disease states are diagnosed in a patient by isolating monocytes from the patient, contacting the monocytes with a conjugate $A_b$-X wherein $A_b$ comprises a ligand that binds to monocytes and X comprises an imaging agent, and quantifying the percentage of monocytes expressing the receptor for the ligand. In another embodiment, the imaging or diagnostic conjugates can be administered to the patient as a diagnostic composition comprising a conjugate and a pharmaceutically acceptable carrier and thereafter monocytes can be collected from the patient to quantify the percentage of monocytes expressing the receptor for the ligand $A_b$. In this embodiment, the composition is typically formulated for parenteral administration and is administered to the patient in an amount effective to enable imaging of monocytes. In another embodiment, disease states can also be diagnosed by administering parenterally to a patient a composition comprising a conjugate or complex of the general formula $A_b$-X where the group $A_b$ comprises a ligand that binds to monocytes and the group X comprises an imaging agent, and quantifying the percentage of monocytes that expresses a receptor for the ligand.

In one embodiment, for example, the imaging agent (e.g., a reporter molecule) can comprise a radiolabeled compound such as a chelating moiety and an element that is a radionuclide, for example a metal cation that is a radionuclide. In another embodiment, the radionuclide is selected from the group consisting of technetium, gallium, indium, and a positron emitting radionuclide (PET imaging agent). In another embodiment, the imaging agent can comprise a chromophore such as, for example, fluorescein, rhodamine, Texas Red, phycoerythrin, Oregon Green, AlexaFluor 488 (Molecular Probes, Eugene, Oreg.), Cy3, Cy5, Cy7, and the like.

Diagnosis typically occurs before treatment. However, in the diagnostic methods described herein, the term "diagnosis" can also mean monitoring of the disease state before, during, or after treatment to determine the progression of the disease state. The monitoring can occur before, during, or after treatment, or combinations thereof, to determine the efficacy of therapy, or to predict future episodes of disease. The imaging can be performed by any suitable imaging method known in the art, such as intravital imaging.

The method disclosed herein can be used for both human clinical medicine and veterinary applications. Thus, the host animal afflicted with the monocyte-mediated disease state and in need of diagnosis or therapy can be a human, or in the case of veterinary applications, can be a laboratory, agricultural, domestic or wild animal. In embodiments where the conjugates are administered to the patient or animal, the conjugates can be administered parenterally to the animal or patient suffering from the disease state, for example, intradermally, subcutaneously, intramuscularly, intraperitoneally, or intravenously. Alternatively, the conjugates can be administered to the animal or patient by other medically useful procedures and effective doses can be administered in standard or prolonged release dosage forms, such as a slow pump. The therapeutic method described herein can be used alone or in combination with other therapeutic methods recognized for the treatment of inflammatory disease states.

In the ligand conjugates of the general formula $A_b$-X, the group $A_b$ is a ligand that binds to monocytes (e.g., activated monocytes) when the conjugates are used to diagnose or treat disease states. Any of a wide number of monocyte-binding ligands can be employed. Acceptable ligands include particularly folate receptor binding ligands, and analogs thereof, and antibodies or antibody fragments capable of recognizing and binding to surface moieties expressed or presented on monocytes. In one embodiment, the monocyte-binding ligand is folic acid, a folic acid analog or another folate receptor binding molecule. In another embodiment the monocyte-binding ligand is a specific monoclonal or polyclonal antibody or an Fab or an scFv (i.e., a single chain variable region) fragment of an antibody capable of binding to monocytes.

In one embodiment, the monocyte-binding ligand can be folic acid, a folic acid analog, or another folate receptor-binding molecule. Analogs of folate that can be used include folinic acid, pteropolyglutamic acid, and folate receptor-binding pteridines such as tetrahydropterins, dihydrofolates, tetrahydrofolates, and their deaza and dideaza analogs. The terms "deaza" and "dideaza" analogs refers to the art recognized analogs having a carbon atom substituted for one or two nitrogen atoms in the naturally occurring folic acid structure. For example, the deaza analogs include the 1-deaza, 3-deaza, 5-deaza, 8-deaza, and 10-deaza analogs. The dideaza analogs include, for example, 1,5dideaza, 5,10-dideaza, 8,10-dideaza, and 5,8-dideaza analogs. The foregoing folic acid analogs are conventionally termed "folates," reflecting their capacity to bind to folate receptors. Other folate receptor-binding analogs include aminopterin, amethopterin (methotrexate), $N^{10}$-methylfolate, 2-deamino-hydroxyfolate, deaza analogs such as 1-deazamethopterin or 3-deazamethopterin, and 3',5'-dichloro-4-amino-4-deoxy-$N^{10}$-methylpteroylglutamic acid (dichloromethotrexate).

In another embodiment, other vitamins can be used as the monocyte-binding ligand. The vitamins that can be used in accordance with the methods described herein include niacin, pantothenic acid, folic acid, riboflavin, thiamine, biotin, vitamin $B_{12}$, vitamins A, D, E and K, other related vitamin molecules, analogs and derivatives thereof, and combinations thereof.

In other embodiments, the monocyte-binding ligand can be any ligand that binds to a receptor expressed or overexpressed on activated monocytes including CD40-, CD16-, CD 14-, CD11b-, and CD62-binding ligands, 5-hydroxytryptamine, macropahge inflammatory protein 1-α, MIP-2, receptor activator of nuclear factor kB ligand antagonists, monocyte chemotactic protein 1-binding ligands, chemokine receptor 5-binding ligands, RANTES-binding ligands, chemokine receptor-binding ligands, and the like.

The monocyte (e.g., activated monocytes) targeted conjugates used for diagnosing or treating disease states mediated by monocytes have the formula $A_b$-X, wherein $A_b$ is a ligand capable of binding to monocytes, and the group X comprises an imaging agent or an immunogen, cytotoxin, or a compound capable of altering monocyte function. In such conjugates wherein the group $A_b$ is folic acid, a folic acid analog, or another folic acid receptor binding ligand, these conjugates are described in detail in U.S. Pat. No. 5,688,488, the specification of which is incorporated herein by reference. That patent, as well as related U.S. Pat. Nos. 5,416,016 and 5,108,921, and related U.S. Patent Application Publication No. 2005/0002942 A1, each incorporated herein by reference, describe methods and examples for preparing conjugates useful in accordance with the methods described herein. The present monocyte-targeted imaging and therapeutic agents can be prepared and used following general protocols described in those earlier patents and patent applications, and by the protocols described herein.

In accordance with another embodiment, there is provided a method of treating disease states mediated by monocytes by administering to a patient suffering from such disease state an effective amount of a composition comprising a conjugate of the general formula $A_b$-X wherein $A_b$ is as defined above and the group X comprises a cytotoxin, an immunogen, or a compound capable of altering monocyte function. In these embodiments, the monocytes can be activated monocytes and the group $A_b$ can be any of the ligands described above. Exemplary of cytotoxic moieties useful for forming conjugates for use in accordance with the methods described herein are clodronate, anthrax, Pseudomonas exotoxin, typically modified so that these cytotoxic moieties do not bind to normal cells, and other toxins or cytotoxic agents including art-recognized chemotherapeutic agents such as adrenocorticoids, alkylating agents, antiandrogens, antiestrogens, androgens, estrogens, antimetabolites such as cytosine arabinoside, purine analogs, pyrimidine analogs, and methotrexate, busulfan, carboplatin, chlorambucil, cisplatin and other platinum compounds, tamoxiphen, taxol, cyclophosphamide, plant alkaloids, prednisone, hydroxyurea, teniposide, and bleomycin, nitrogen mustards, nitrosureas, vincristine, vinblastine, MEK kinase inhibitors, MAP kinase pathway inhibitors, PI-3-kinase inhibitors, mitochondrial perturbants, NFκB pathway inhibitors, proteosome inhibitors, pro-apoptotic agents, glucocorticoids, such as prednisolone, flumethasone, dexamethasone, and betamethasone, indomethacin, diclofenac, proteins such as pokeweed, saporin, momordin, and gelonin, non-steroidal anti-inflammatory drugs (NSAIDs), protein synthesis inhibitors, didemnin B, verrucarin A, geldanamycin, and the like. Such toxins or cytotoxic compounds can be directly conjugated to the monocyte-binding ligand, for example, folate or another folate receptor-binding ligand, or they can be formulated in liposomes or other small particles which themselves are targeted as conjugates of the monocyte-binding ligand typically by covalent linkages to component phospholipids.

Similarly, when the group X comprises a compound capable of altering a monocyte function, for example, a cytokine such as IL-10 or IL-11, the compound can be covalently linked to the targeting ligand $A_b$, for example, a folate receptor-binding ligand or a monocyte-binding antibody or antibody fragment directly, or the monocyte function altering compound can be encapsulated in a liposome which is itself targeted to monocytes by pendent monocyte targeting ligands $A_b$ covalently linked to one or more liposome components.

In another embodiment, conjugates $A_b$-X where X is an immunogen or a compound capable of altering monocyte function, can be administered in combination with a cytotoxic compound. The cytotoxic compounds listed above are among the compounds suitable for this purpose.

In another method of treatment embodiment, the group X in the monocyte targeted conjugate $A_b$-X, comprises an immunogen, the ligand-immunogen conjugates being effective to "label" the population of monocytes responsible for disease pathogenesis in the patient suffering from the disease for specific elimination by an endogenous immune response or by co-administered antibodies. The use of ligand-immunogen conjugates in the method of treatment described herein works to enhance an immune response-mediated elimination of the monocyte population that expresses the ligand receptor. Such elimination can be effected through an endogenous immune response or by a passive immune response effected by co-administered antibodies.

The methods of treatment involving the use of ligand-immunogen conjugates are described in U.S. Patent Application Publication Nos. U.S. 2001/0031252 A1 and U.S. 2002/0192157 A1, and PCT Publication No. WO 2004/100983, each incorporated herein by reference.

The endogenous immune response can include a humoral response, a cell-mediated immune response, and any other immune response endogenous to the host animal, including complement-mediated cell lysis, antibody-dependent cell-mediated cytotoxicity (ADCC), antibody opsonization leading to phagocytosis, clustering of receptors upon antibody binding resulting in signaling of apoptosis, antiproliferation, or differentiation, and direct immune cell recognition of the delivered immunogen (e.g., an antigen or a hapten). It is also contemplated that the endogenous immune response may employ the secretion of cytokines that regulate such processes as the multiplication and migration of immune cells. The endogenous immune response may include the participation of such immune cell types as B cells, T cells, including helper and cytotoxic T cells, macrophages, natural killer cells, neutrophils, LAK cells, and the like.

The humoral response can be a response induced by such processes as normally scheduled vaccination, or active immunization with a natural antigen or an unnatural antigen or hapten, e.g., fluorescein isothiocyanate (FITC), with the unnatural antigen inducing a novel immunity. Active immunization involves multiple injections of the unnatural antigen or hapten scheduled outside of a normal vaccination regimen to induce the novel immunity. The humoral response may also result from an innate immunity where the host animal has a natural preexisting immunity, such as an immunity to α-galactosyl groups.

Alternatively, a passive immunity may be established by administering antibodies to the host animal such as natural antibodies collected from serum or monoclonal antibodies that may or may not be genetically engineered antibodies, including humanized antibodies. The utilization of a particular amount of an antibody reagent to develop a passive immunity, and the use of a ligand-immunogen conjugate wherein the passively administered antibodies are directed to the immunogen, would provide the advantage of a standard set of reagents to be used in cases where a patient's preexisting antibody titer to potential antigens is not therapeutically useful. The passively administered antibodies may be "co-administered" with the ligand-immunogen conjugate, and co-administration is defined as administration of antibodies at a time prior to, at the same time as, or at a time following administration of the ligand-immunogen conjugate.

The preexisting antibodies, induced antibodies, or passively administered antibodies will be redirected to the monocytes by preferential binding of the ligand-immunogen conjugates to the monocyte cell populations, and such pathogenic cells are killed by complement-mediated lysis, ADCC, antibody-dependent phagocytosis, or antibody clustering of receptors. The cytotoxic process may also involve other types of immune responses, such as cell-mediated immunity.

Acceptable immunogens for use in preparing the conjugates used in the method of treatment described herein are immunogens that are capable of eliciting antibody production in a host animal or that have previously elicited antibody production in a host animal, resulting in a preexisting immunity, or that constitute part of the innate immune system. Alternatively, antibodies directed against the immunogen may be administered to the host animal to establish a passive immunity. Suitable immunogens for use in the invention include antigens or antigenic peptides against which a preexisting immunity has developed via normally scheduled vaccinations or prior natural exposure to such agents such as polio virus, tetanus, typhus, rubella, measles, mumps, pertussis, tuberculosis and influenza antigens, and α-galactosyl groups. In such cases, the ligand-immunogen conjugates will be used to redirect a previously acquired humoral or cellular immunity to a population of monocytes in the host animal for elimination of the monocytes.

Other suitable immunogens include antigens or antigenic peptides to which the host animal has developed a novel immunity through immunization against an unnatural antigen or hapten, for example, fluorescein isothiocyanate (FITC) or dinitrophenyl, and antigens against which an innate immunity exists, for example, super antigens and muramyl dipeptide.

The monocyte-binding ligands and immunogens, cytotoxic agents, compounds capable of altering monocyte function, or imaging agents, as the case may be in forming conjugates for use in accordance with the methods described herein can be conjugated by using any art-recognized method for forming a complex. This can include covalent, ionic, or hydrogen bonding of the ligand to the immunogen, either directly or indirectly via a linking group such as a divalent linker. The conjugate is typically formed by covalent bonding of the ligand to the targeted entity through the formation of amide, ester or imino bonds between acid, aldehyde, hydroxy, amino, or hydrazo groups on the respective components of the complex or, for example, by the formation of disulfide bonds. Methods of linking monocyte-binding ligands to immunogens, cytotoxic agents, compounds capable of altering monocyte function, or imaging agents are described in U.S. Patent Application Publication No. 2005/0002942 A1 and PCT Publication No. WO 2006/012527, each incorporated herein by reference.

Alternatively, as mentioned above, the ligand complex can be one comprising a liposome wherein the targeted entity (that is, the imaging agent, or the immunogen, cytotoxic agent or monocyte function-altering agent) is contained within a liposome which is itself covalently linked to the monocyte-binding ligand. Other nanoparticles, dendrimers, derivatizable polymers or copolymers that can be linked to therapeutic or imaging agents useful in the treatment and diagnosis of monocyte-mediated diseases can also be used in targeted conjugates.

In one embodiment of the invention the ligand is folic acid, an analog of folic acid, or any other folate receptor binding molecule, and the folate ligand is conjugated to the targeted entity by a procedure that utilizes trifluoroacetic anhydride to prepare γ-esters of folic acid via a pteroyl azide intermediate. This procedure results in the synthesis of a folate ligand, conjugated to the targeted entity only through the γ-carboxy group of the glutamic acid groups of folate. Alternatively, folic acid analogs can be coupled through the α-carboxy moiety of the glutamic acid group or both the α and γ carboxylic acid entities.

The therapeutic methods described herein can be used to slow the progress of disease completely or partially. Alternatively, the therapeutic methods described herein can eliminate or prevent reoccurrence of the disease state.

The conjugates used in accordance with the methods described herein of the formula $A_b$-X are used in one aspect to formulate therapeutic or diagnostic compositions, for administration to a patient, wherein the compositions comprise effective amounts of the conjugate and an acceptable carrier therefor. Typically such compositions are formulated for parenteral use. The amount of the conjugate effective for use in accordance with the methods described herein depends on many parameters, including the nature of the disease being treated or diagnosed, the molecular weight of the conjugate, its route of administration and its tissue distribution, and the possibility of co-usage of other therapeutic or diagnostic agents. The effective amount to be administered to a patient is typically based on body surface area, patient weight and physician assessment of patient condition. An effective amount can range from about to 1 ng/kg to about 1 mg/kg, more typically from about 1 μg/kg to about 500 μg/kg, and most typically from about 1 μg/kg to about 100 μg/kg.

Any effective regimen for administering the ligand conjugates can be used. For example, the ligand conjugates can be administered as single doses, or they can be divided and administered as a multiple-dose daily regimen. Further, a staggered regimen, for example, one to three days per week can be used as an alternative to daily treatment, and such an intermittent or staggered daily regimen is considered to be equivalent to every day treatment and within the scope of this disclosure. In one embodiment, the patient is treated with multiple injections of the ligand conjugate wherein the targeted entity is an immunogen or a cytotoxic agent or a compound capable of altering monocyte function to eliminate the population of pathogenic monocytes. In one embodiment, the patient is treated, for example, injected multiple times with the ligand conjugate at, for example, 12-72 hour intervals or at 48-72 hour intervals. Additional injections of the ligand conjugate can be administered to the patient at intervals of days or months after the initial injections, and the additional injections prevent recurrence of disease. Alternatively, the ligand conjugates may be administered prophylactically to prevent the occurrence of disease in patients known to be disposed to development of monocyte-mediated disease states. In one embodiment, more than one type of ligand conjugate can be used, for example, the host animal may be pre-immunized with fluorescein isothiocyanate and dinitrophenyl and subsequently treated with fluorescein isothiocyanate and dinitrophenyl linked to the same or different monocyte targeting ligands in a co-dosing protocol.

The ligand conjugates are administered in one aspect parenterally and most typically by intraperitoneal injections, subcutaneous injections, intramuscular injections, intravenous injections, intradermal injections, or intrathecal injections. The ligand conjugates can also be delivered to a patient using an osmotic pump. Examples of parenteral dosage forms include aqueous solutions of the conjugate, for example, a solution in isotonic saline, 5% glucose or other well-known pharmaceutically acceptable liquid carriers such as alcohols, glycols, esters and amides. The parenteral compositions for use in accordance with this invention can be in the form of a reconstitutable lyophilizate comprising the one or more doses of the ligand conjugate. In another aspect, the ligand conjugates can be formulated as one of any of a number of prolonged release dosage forms known in the art such as, for example, the biodegradable carbohydrate matrices described in U.S. Pat. Nos. 4,713,249; 5,266,333; and 5,417,982, the disclosures of which are incorporated herein by reference. The ligand conjugates can also be administered topically such as in an ointment or a lotion, for example, for treatment of inflammations of the skin.

In any of the embodiments discussed above, the monocytes can be activated monocytes or other monocyte populations that cause disease states. The following examples are illustrative embodiments only and are not intended to be limiting.

EXAMPLE 1

Materials

Fmoc-protected amino acid derivatives, trityl-protected cysteine 2-chlorotrityl resin (H-Cys(Trt)-2-ClTrt resin #04-12-2811), Fmoc-lysine(4-methyltrityl) wang resin, 2-(1H-benzotriaxol-1-yl)-1,1,3,3-tetramethyluronium hexafluorophosphage (HBTU) and N-hydroxybenzotriazole were purchased from Novabiochem (La Jolla, Calif.). $N^{10}$-trifluoroacetylpteroic acid was purchased from Sigma, St. Louis, Mo. All anti-mouse and anti-human antibodies were purchased from Caltag Laboratories, Burlingame, Calif. Folate-R-Phycoerytherin, Folate-Alexa Fluor 488, Folate-Texas Red, and Folate-Fluorescein and Folate-cysteine were synthesized as described. Tritium ($^3$H)-labeled folic acid was obtained from American Radiolabeled Chemicals (St. Louis, Mo.).

EXAMPLE 2

Synthesis of Folate-Cysteine

Standard Fmoc peptide chemistry was used to synthesize folate-cysteine with the cysteine attached to the γ-COOH of folic acid. The sequence Cys-Glu-Pteroic acid (Folate-Cys) was constructed by Fmoc chemistry with HBTU and N-hydroxybenzotriazole as the activating agents along with diisopropyethylamine as the base and 20% piperidine in dimethylformamide (DMF) for deprotection of the Fmoc groups. An α-t-Boc-protected N-α-Fmoc-L-glutamic acid was linked to a trityl-protected Cys linked to a 2-Chlorotrityl resin. $N^{10}$-trifluoroacetylpteroic acid was then attached to the γ-COOH of Glu. The Folate-Cys was cleaved from the resin using a 92.5% trifluoroacetic acid-2.5% water-2.5% triisopropylsilane-2.5% ethanedithio solution. Diethyl ether was used to precipitate the product, and the precipitate was collected by centrifugation. The product was washed twice with diethyl ether and dried under vacuum overnight. To remove the $N^{10}$-trifluoracetyl protecting group, the product was dissolved in a 10% ammonium hydroxide solution and stirred for 30 min at room temperature. The solution was kept under a stream of nitrogen the entire time in order to prevent the cysteine from forming disulfides. After 30 minutes, hydrochloric acid was added to the solution until the compound precipitated. The product was collected by centrifugation and lyophilized. The product was analyzed and confirmed by mass spectroscopic analysis (MW 544, M$^+$ 545).

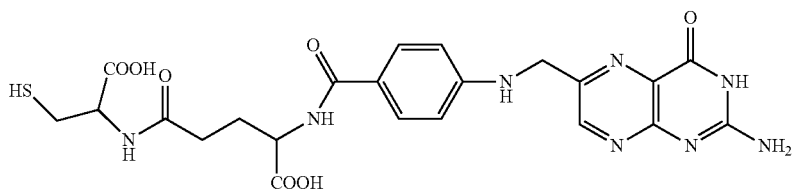

Cys--g-Glu-Pteroic Acid
MW 544.54

EXAMPLE 3

Synthesis of Folate-Cys-Alexafluor 488

AlexaFluor 488 C$_5$-maleimide (Molecular Probes, Eugene, Oreg.) was dissolved in dimethyl sulfoxide (DMSO) (0.5 mg in 50 µl DMSO). A 1.5 molar equivalent (0.57 mg) of Folate-Cys was added to the solution and mixed for 4 hours at room temperature. Folate-Cys-AlexaFluor 488 (Folate-AlexaFluor) was purified by reverse-phase HPLC on a C18 column at a flow rate of 1 ml/min. The mobile phase, consisting of 10 mM NH$_4$HCO$_3$ buffer, pH 7.0 (eluent A) and acetonitrile (eluent B), was maintained at a 99:1 A:B ratio for the first minute and then changed to 1:99 A:B in a linear gradient over the next 29 minutes. Folate-Cys-AlexaFluor 488 eluted at 20 minutes. The product was confirmed by mass spectroscopy and the biologic activity was confirmed by fluorescence measurement of its binding to cell surface folate receptors on folate receptor positive M109 cells in culture.

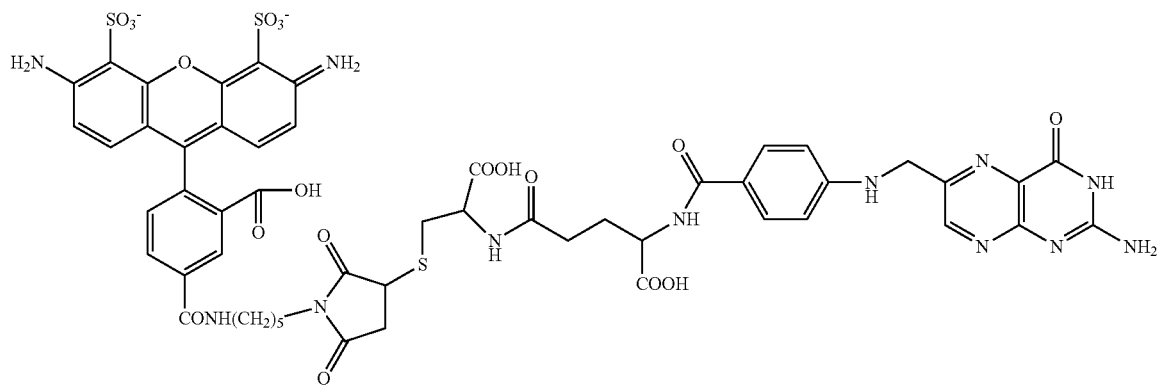

Alexa Fluor 488 - Cys--γ-Glu-Pteroic Acid
MW 1242.21

EXAMPLE 4

Synthesis of Folate-Cys-Texas Red

Texas Red $C_2$-maleimide (Molecular Probes, Eugene, Oreg.) was dissolved in dimethyl sulfoxide (DMSO) (1 mg in 200 μl DMSO). A 1.4 molar equivalent (1 mg) of Folate-Cys was added to the solution and mixed for 4 hours at room temperature. Folate-Cys-Texas Red (Folate-Texas Red) was purified by reverse-phase HPLC on a C18 column at a flow rate of 1 ml/min. The mobile phase, consisting of 10 mM $NH_4HCO_3$ buffer, pH 7.0 (eluent A) and acetonitrile (eluent B), was maintained at a 99:1 A:B ratio for the first five minutes and then changed to 70:30 A:B in a linear gradient over the next 30 minutes followed by a 1:99 A:B linear gradient over the last 15 minutes. Folate-Cys-Texas Red eluted as two isomer peaks at 44.5 and 45.8 minutes. The product was confirmed by mass spectroscopy and the biologic activity was confirmed by fluorescence measurement of its binding to cell surface folate receptors on folate receptor positive M109 cells in culture.

EXAMPLE 5

Synthesis of Folate-Oregon Green 514

Standard Fmoc peptide chemistry was used to synthesize a folate peptide linked to Oregon Green (Molecular Probes, Eugene, Oreg.) attached to the γ-COOH of folic acid. The sequence Lys-Glu-Pteroic acid (Folate-Cys) was constructed by Fmoc chemistry with HBTU and N-hydroxybenzotriazole as the activating agents along with diisopropyethylamine as the base and 20% piperidine in dimethylformamide (DMF) for deprotection of the Fmoc groups. An α-t-Boc-protected N-α-Fmoc-L-glutamic acid followed by a $N^{10}$-trifluoroacetylpteroic acid was linked to a Fmoc-protected lysine wang resin containing a 4-methyltrityl protecting group on the ε-amine. The methoxytrityl protecting group on the ε-amine of lysine was removed with 1% trifluoroacetic acid in dichloromethane to allow attachment of Oregon Green (Folate-Oregon Green). A 1.5 molar equivalent of Oregon Green carboxylic acid, succinimidyl ester was reacted overnight with the peptide and then washed thoroughly from the peptide resin beads. The Folate-Oregon Green was then cleaved from the resin with a 95% trifluoroacetic acid-2.5% water-2.5% triisopropylsilane solution.

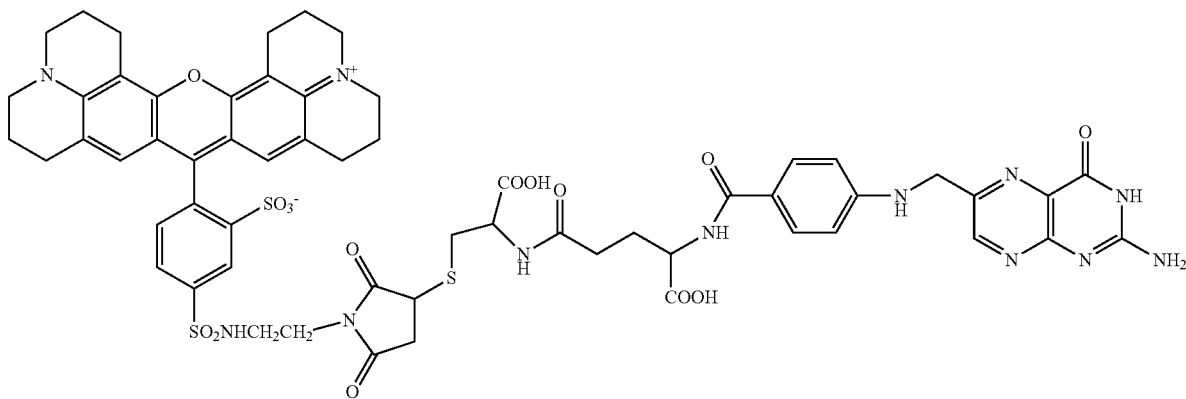

Texas Red - Cys--γ-Glu-Pteroic Acid
MW 1273.37

Diethyl ether was used to precipitate the product, and the precipitant was collected by centrifugation. The product was washed twice with diethyl ether and dried under vacuum overnight. To remove the $N^{10}$-trifluoracetyl protecting group, the product was dissolved in a 10% ammonium hydroxide solution and stirred for 30 min at room temperature. The product was precipitated with combined isopropanol and ether, and the precipitant was collected by centrifugation.

ered saline (PBS), pH 7.4. The solution was allowed to react overnight at 4° C. and the labeled protein (Mr~260 kDa) was purified by gel filtration chromatography using a G-15 desalting column. The folate labeling was confirmed by fluorescence microscopy of M109 cells incubated with folate-phycoerythrin in the presence and absence of 100-fold excess of folic acid. After a 1-h incubation and 3 cells washes with PBS, the treated cells were intensely fluores-

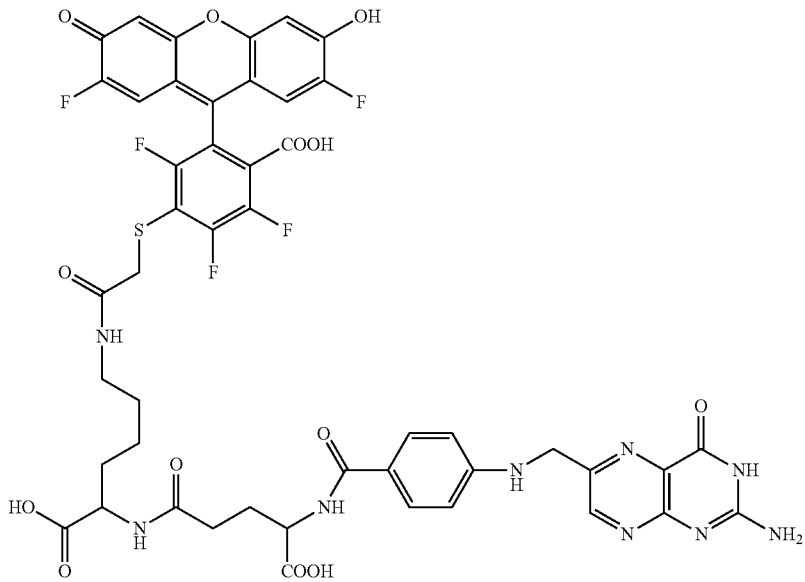 [SMILES: Nc1nc2ncc(CNc3ccc(C(=O)NC(CCC(=O)NC(CCCCNC(=O)CSc4c(F)c(F)c(C(=O)O)c(-c5c6cc(F)c(=O)cc-6oc6cc(O)c(F)cc56)c4F)C(=O)O)C(=O)O)cc3)nc2c(=O)[nH]1]

EXAMPLE 6

Synthesis of Folate-R-Phycoerythrin

Folate-phycoerythrin was synthesized by following a procedure published by Kennedy M. D. et al. in *Pharmaceutical Research*, Vol. 20(5); 2003. Briefly, a 10-fold excess of folate-cysteine was added to a solution of R-phycoerythrin pyridyldisulfide (Sigma, St. Louis, Mo.) in phosphate buffcent, while the sample in the presence of excess folic acid showed little cellular fluorescence.

EXAMPLE 7

Synthesis of Folate-Fluorescein

Folate-FITC was synthesized as described by Kennedy, M. D. et al. in *Pharmaceutical Research*, Vol. 20(5); 2003.

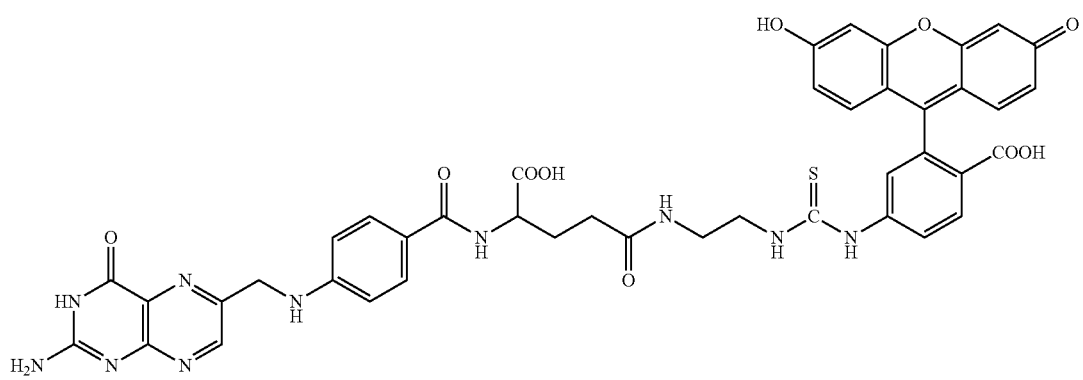

Folate-EDA-FITC
MW 888.90

EXAMPLE 8

Synthesis of Folate-D-R-D-D-C-Prednisolone

Standard Fmoc peptide chemistry was used to synthesize folate-aspartate-arginine-aspartate-aspartate-cysteine (Folate-Asp-Arg-Asp-Asp-Cys, Folate-D-R-D-D-C) with the amino acid spacer attached to the γ-COOH of folic acid. The sequence Cys-Asp-Asp-Arg-Asp-Glu-Pteroic acid (Folate-Asp-Arg-Asp-Asp-Cys) was constructed by Fmoc chemistry with HBTU and N-hydroxybenzotriazole as the activating agents along with diisopropyethylamine as the base and 20% piperidine in dimethylformamide (DMF) for deprotection of the Fmoc groups. Fmoc-D-Asp(OtBu)-OH was linked to a trityl-protected Cys linked to a 2-Chlorotrityl resin. A second Fmoc-D-Asp(OtBu)-OH followed by Fmoc-Arg(Pbf)-OH, Fmoc-D-Asp(OtBu)-OH and Fmoc-Glu-OtBu were added successively to the resin. $N^{10}$-trifluoroacetylpteroic acid was then attached to the γ-COOH of Glu. The Folate-Asp-Arg-Asp-Asp-Cys was cleaved from the resin using a 92.5% trifluoroacetic acid-2.5% water-2.5% triisopropylsilane-2.5% ethanedithio solution. Diethyl ether was used to precipitate the product, and the precipitant was collected by centrifugation. The product was washed twice with diethyl ether and dried under vacuum overnight. To remove the $N^{10}$-trifluoroacetyl protecting group, the product was dissolved in a 10% ammonium hydroxide solution and stirred for 30 min at room temperature. The solution was kept under a stream of nitrogen the entire time in order to prevent the cysteine from forming disulfides. After 30 minutes, hydrochloric acid was added to the solution until the compound precipitated. The product was collected by centrifugation and lyophilized. The product was analyzed and confirmed by mass spectroscopic analysis (MW 1046).

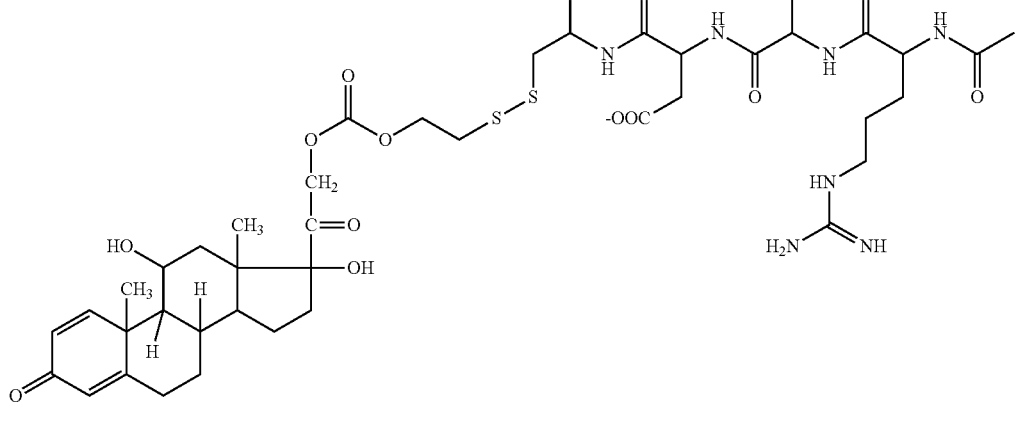

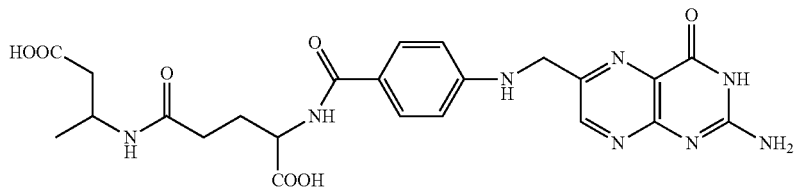

Prednisolone-Cys-Asp-Asp-Arg-Asp-γ-Glu-Pteroic Acid
MW 1507.5

EXAMPLE 9

Synthesis of Folate-Indomethacin

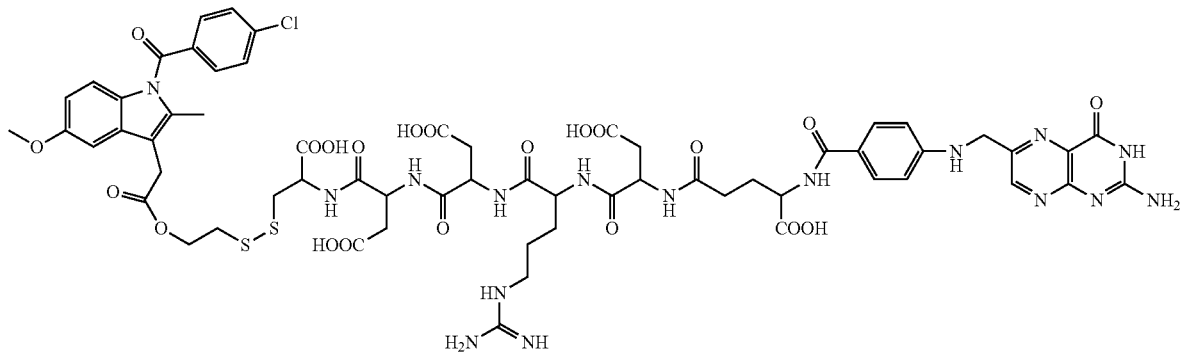

Indomethacin-Cys-Asp-Asp-Arg-Asp-γ-Glu-Pteroic Acid
MW 1462

2-(2-Pyridyldithio)ethanol was synthesized by dissolving 1.5 equivalents of Aldrithiol (Sigma, St. Louis, Mo.) with 6 equivalents of 4-dimethylaminopyridine (DMAP) in dichloromethane (DCM). The solution was purged with nitrogen and 1 equivalent of mercaptoethanol was added dropwise to the Aldrithiol solution over the course of 15 minutes. The reaction proceeded at room temperature for 30 minutes at which time no odor of mercaptoethanol remained. The reaction was diluted 100-fold with DCM and 5 g of activated carbon was added per gram of Aldrithiol. The reaction mixture was filtered and the solvent removed. The mixture was resuspended in 70:30 (Petroleum ether:Ethylacetate (EtOAc)) and purified by flash chromatography on a 60 Å silica gel column. The product was monitored by thin layer chromatography and collected.

Folate-indomethacin was synthesized following a modified method published by Kalgutkar et al. in the *Journal of Med. Chem.* 2000, 43; 2860-2870 where the anti-inflammatory (indomethacin) was linked through an ester bond with the 2-(2-Pyridyldithio)ethanol. Briefly, 1 equivalent of indomethacin was dissolved in DCM along with 0.08 equivalents DMAP, 1.1 equivalents 2-(2-Pyridyldithio) ethanol and 1.1 equivalents 1,3-dicyclohexyl-carbodiimide. The reaction proceeded at room temperature for 5 hours. The reaction was purified by chromatography on silica gel (EtOAc:hexanes, 20:80). One equivalent of the purified compound was dissolved in DMSO and to it were added 1.5 equivalents of the folate-Asp-Arg-Asp-Asp-Cys peptide. The resulting solution was reacted for 3 hours at room temperature followed by purification using a HPLC reverse-phase C18 column at a flow rate of 1 ml/min. The mobile phase, consisting of 10 mM $NH_4HCO_3$ buffer, pH 7.0 (eluent A) and acetonitrile (eluent B), was maintained at a 99:1 A:B ratio for the first five minutes and then changed to 70:30 A:B in a linear gradient over the next 30 minutes. The recovered final product was confirmed by mass spectrometry.

EXAMPLE 10

Synthesis of Folate-Diclofenac

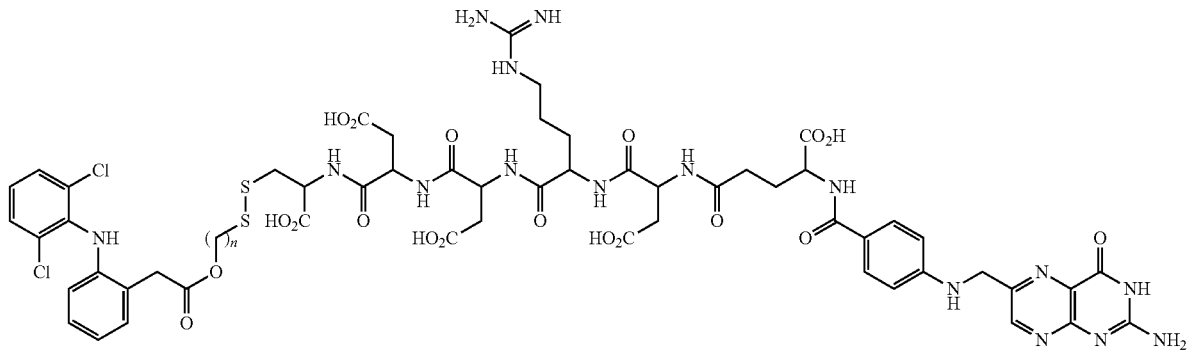

Diclofenac-Cys-Asp-Asp-Arg-Asp-γ-Glu-Pteroic Acid
MW 1386

Folate-diclofenac was synthesized by the method described in Example 9 except that diclofenac was used in place of indomethicin. In various embodiments, n=1, 2, or 3, and where n is illustratively 2.

EXAMPLE 11

Synthesis of Folate-Cys-Prednisolone

The folate glucocorticoid conjugate of prednisolone was prepared as follows. A 1.1 molar equivalent of prednisone was dissolved in tetrahydrofuran (THF). In a separate vial, a 0.7 molar equivalent of dimethylaminopyridine, 1 molar equivalent of tri(hydroxyethyl)amine and 1 molar equivalent of the linker (synthesis described in PCT Publication No. WO 2006/012527, incorporated herein by reference) were dissolved in dichloromethane. An approximately equal volume of both solutions were combined, mixed and reacted at room temperature for 4 hours. The reaction was monitored by thin layer chromatography using 40:10:1 (Dichloromethane:Acetonitrile: Methanol). The product had an $R_f$=0.52.

The product was purified on a silica column (Silica 32-63, 60 Å) using the same ratio of solvents. The recovered product was dried in preparation for conjugation to a folate-peptide. The derivatized glucocorticoid was dissolved in DMSO, to which was added a 1.5 molar equivalent of either the folate-cys or folate-Asp-Arg-Asp-Asp-Cys peptide. The resulting solution was reacted for 3 hours at room temperature followed by purification using a HPLC reverse-phase C18 column at a flow rate of 1 ml/min. The mobile phase, consisting of 10 mM $NH_4HCO_3$ buffer, pH 7.0 (eluent A) and acetonitrile (eluent B), was maintained at a 99:1 A:B ratio for the first minute and then changed to 1:99 A:B in a linear gradient over the next 39 minutes. The folate-glucocorticoid conjugate eluted at approximately 26 minutes. The recovered final product was confirmed by mass spectrometry.

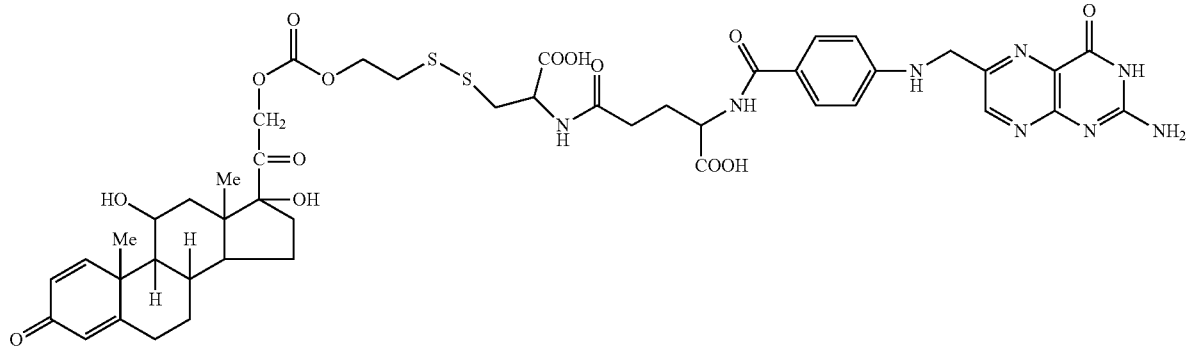

Prednisolone-Cys--γ-Glu-Pteroic Acid
MW 1007.10

EXAMPLE 12

Synthesis of Folate-Cys-Dexamethasone

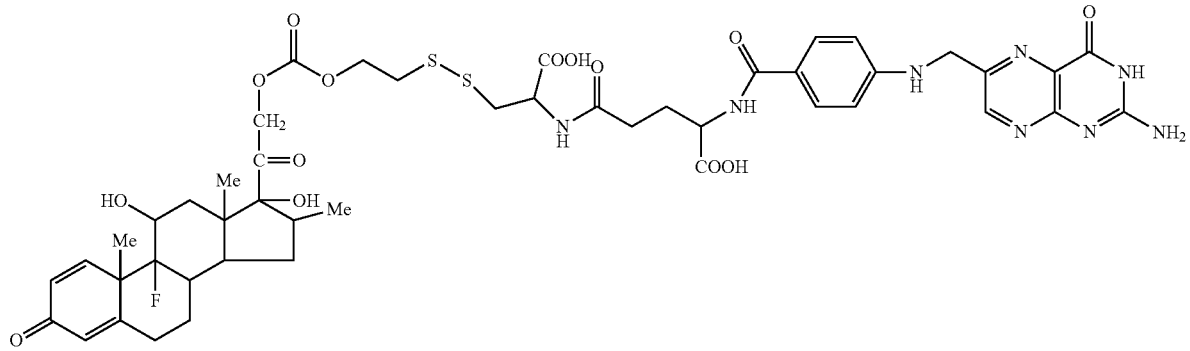

Dexamethasone-Cys--γ-Glu-Pteroic Acid
MW 1039.11

Folate-cys-dexamethasone was synthesized by a procedure similar to that described in Example 11 except that the glucocorticoid was dexamethasone.

EXAMPLE 13

Synthesis of Folate-Cys-Flumethasone

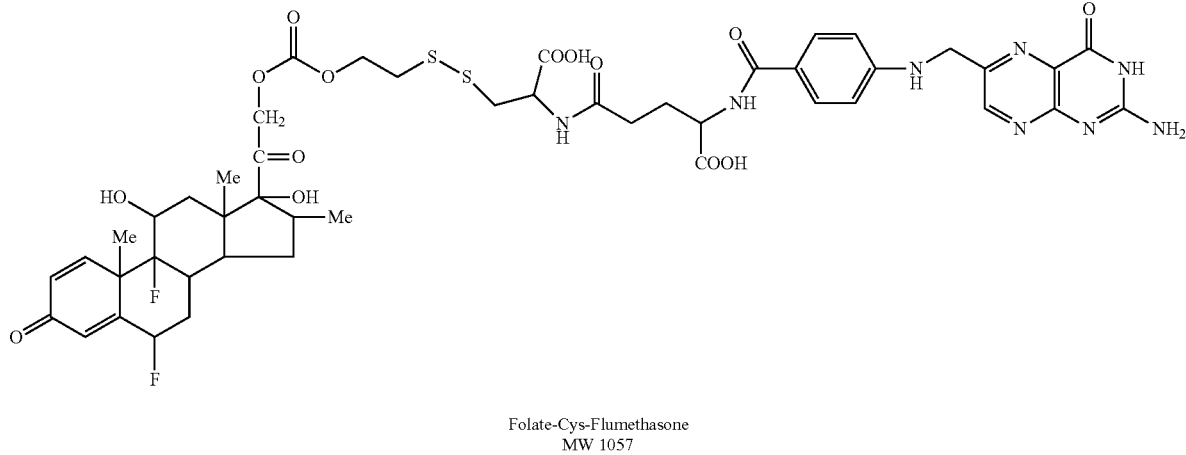

Folate-Cys-Flumethasone
MW 1057

Folate-cys-flumethasone was synthesized by a procedure similar to that described in Example 11 except that the glucocorticoid was flumethasone.

EXAMPLE 14

Isolation of Peripheral Blood Mononuclear Cells (PBMC)

An 8-10 ml sample of whole blood was collected in EDTA anticoagulant tubes. PBMCs were isolated from the blood samples using Ficoll-Paque Plus (Amersham Biosciences, Piscataway, N.J.) and by following the manufacture's provided protocol. Briefly, the blood sample was diluted 50:50 with a balanced salt solution (described below). 8 mL of Ficoll-Paque Plus was added to a 50 ml conical centrifuge tube. The diluted blood sample (approximately 16-20 ml) was layered on top of the Ficoll gradient. The sample was centrifuged at 400×g for 30 minutes at room temperature. Following centrifugation, the plasma layer (top clear layer) was removed using a pipette leaving the lymphocyte/monocyte layer undisturbed. The hazy cell layer immediately below the plasma layer was removed, being careful to remove the entire cell interface but a minimum amount of the Ficoll layer. The isolated cells were put into a sterile 50 ml conical centrifuge tube and diluted 3-fold (vol/vol) using the balanced salt solution. The resulting cell solution was gently mixed and centrifuged at 100×g for 10 minutes at room temperature to pellet the cells. The supernatant was removed and the cells were resuspended in folate deficient RPMI 1640 medium supplemented with 10% heat-inactivated FBS, penicillin (100 IU/ml) and streptomycin (100 µg/ml). Cells were seeded in microcentrifuge tubes or microscopy chambers as dictated by the experiment.

EXAMPLE 15

Balanced Salt Solution

Balanced Salt Solution Preparation (as Prepared by Amersham Biosciences)

| Solution A | | Concentration. (g/L) |
|---|---|---|
| Anhydrous D-glucose | 0.1 percent | 1.0 |
| $CaCl_2 \times 2H_2O$ | $5.0 \times 10^{-5}M$ | 0.0074 |
| $MgCl_2 \times 6H_2O$ | $9.8 \times 10^{-4}M$ | 0.1992 |
| KCl | $5.4 \times 10^{-3}M$ | 0.4026 |
| TRIS | 0.145M | 17.565 |

Dissolve in approximately 950 ml distilled water and add 10 N HCl until pH is 7.6 before adjusting the volume to 1 L.

| Solution B | Concentration (g/L) |
|---|---|
| NaCl | 0.14M | 8.19 |

To prepare the balanced salt solution mix 1 volume Solution A with 9 volumes Solution B.

EXAMPLE 16

Ligand Binding

All binding experiments were conducted on ice or in a 4° C. cold room unless indicated otherwise. Folate conjugate and $^3$H-folic acid binding studies were performed by incubating cells with a 100 nM concentration of the indicated folate dye conjugate for 45 minutes. Competition samples were prepared by pre-incubating the appropriate samples with a 100-fold excess concentration of folic acid (10 μM) five minutes prior to adding the folate dye conjugate. An acidic wash to strip cell-surface bound folate conjugates was performed on indicated samples by washing the cell sample with a 150 mM NaCl solution adjusted to pH 3.5 with acetic acid. All antibody labeling was optimized by titration. Optimal labeling was most often achieved with a 1/1000-1/10,000 dilution of the manufacture's stock antibody solution. After cells were labeled with folate dye conjugates and/or antibodies, the samples were washed twice with PBS to remove non-specific binding. Analysis of folate conjugate binding and/or antibody binding was analyzed by confocal microscopy or by flow cytometry (FCS Calibur, BD, Franklin Lakes, N.J.). After washing $^3$H-folic acid samples to remove non-specific binding, cells were dissolved in 0.25M NaOH and radioactivity was counted on a scintillation counter.

EXAMPLE 17

Synthesis of Folate Resonance Energy Tranfer Reporter

Compound 1 was prepared by following standard Fmoc chemistry on an acid-sensitive trityl resin loaded with Fmoc-L-Cys (Trt)-OH, as described previously (adapted to the shown peptide sequence). The crude compound 1 was purified by HPLC using a VYDAC protein and peptide C18 column. The HPLC-purified 1 was then reacted with tetraethylrhodamine methanethiosulfonate (Molecular Probes, Eugene, Oreg.) in DMSO to afford compound 2, in the presence of diisopropylethylamine (DIPEA). The desired product was isolated from the reaction mixture by preparative HPLC as described above. The final conjugation was performed by mixing excess DIPEA with 2 (in DMSO) followed by addition of BODIPY FL NHS ester (Molecular Probes, Eugene, Oreg.). Compound 3 was then isolated from this reaction mixture by preparative HPLC.

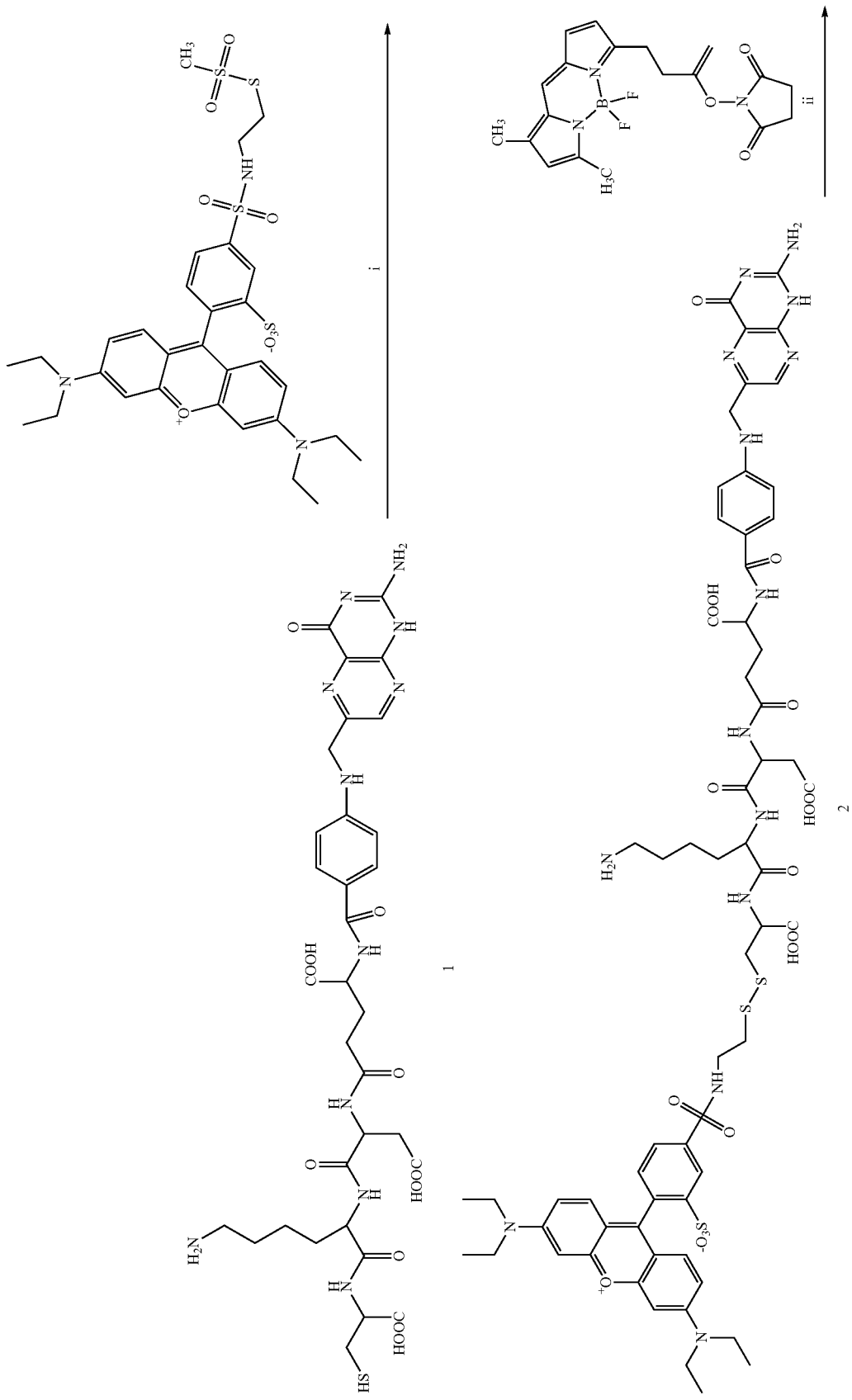

-continued
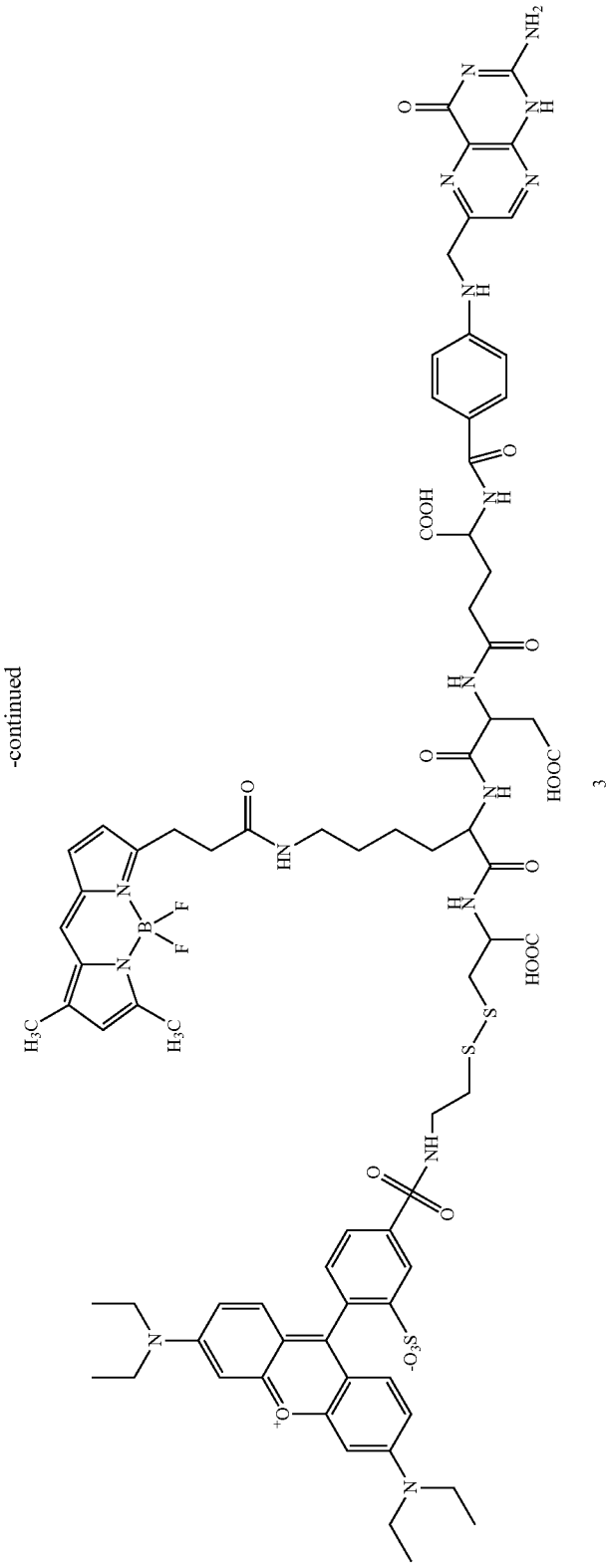

EXAMPLE 18

Laser Imaging

Fluorescence resonance energy transfer (FRET) imaging of monocytes to determine uptake of folate-linked imaging agents will be carried out using a confocal microscopy. An Olympus IX-70 inverted microscopy (Olympus, USA) equipped with an Olympus FW300 scanning box and an Olympus 60X/1.2 NA water objective will be used to image the cells. Separate excitation lines and emission filters will be used for each fluorochrome (BODIPY FL, 488 nm (excitation) and 520/40 nm (emission); rhodamine, 543 nm (excitation) and 600/70 nm (emission)). Two laser sources with 543 nm (He—Ne) and 488 nm (Argon) wavelength can be used to excite BODIPY FL and rhodamine separately to obtain two color images when needed. Confocal images can be acquired with a size of 512×512 pixels at 2.7 second scan time and images can be processed using FluoView (Olympus) software.

EXAMPLE 19

Liposome Preparation

Liposomes were prepared following methods by Leamon et al. in *Bioconjugate Chemistry* 2003, 14, 738-747. Briefly, lipids and cholesterol were purchased from Avanti Polar Lipids (Alabaster, Ala.). Folate-targeted liposomes consisted of 40 mole % cholesterol, either 4 mole % or 6 mole % polyethyleneglycol (Mr~2000)-derivatized phosphatidylethanolamine (PEG2000-PE, Nektar Ala., Huntsville, Ala.), either 0.03 mole % or 0.1 mole % folate-cysteine-PEG3400-PE and the remaining mole % was composed of egg phosphatidylcholine. Non-targeted liposomes were prepared identically with the absence of folate-cysteine-PEG3400-PE. Lipids in chloroform were dried to a thin film by rotary evaporation and then rehydrated in PBS containing the drug. Rehydration was accomplished by vigorous vortexing followed by 10 cycles of freezing and thawing. Liposomes were then extruded 10 times through a 50 nm pore size polycarbonate membrane using a high-pressure extruder (Lipex Biomembranes, Vancouver, Canada).

EXAMPLE 20

Synthesis of Folate-Pokeweed

Pokeweed antiviral protein was purchased from Worthington Biochemical Corporation (Lakewood, N.J.). N-succinimidyl-3-[2-pyridyldithio] propionate (SPDP; Pierce, Rockford, Ill.) was dissolved in dimethylformamide (9.6 mM). While on ice, a 5 fold molar excess of SPDP (~170 nmoles) was added to the pokeweed solution (1 mg/ml PBS, MW~29,000). The resulting solution was gently mixed and allowed to react for 30 minutes at room temperature. The non-conjugated SPDP was removed using a centrifuge molecular weight concentrator (MWCO 10,000) (Millipore, Billerica, Mass.). The resulting protein solution was resuspended in PBS containing 10 mM EDTA to a final volume of 1 mL. Approximately a 60 fold molar excess of folate-Asp-Arg-Asp-Asp-Cys peptide (2000 nmoles) was added to the protein solution and allowed to react for 1 hour. The non-reacted folate-Asp-Arg-Asp-Asp-Cys peptide was removed using the centrifuge concentrators as previously described. The protein was washed twice by resuspending the protein in PBS and repeating the protein concentration by centrifugation.

EXAMPLE 21

Synthesis of Folate-Saporin

The protein saporin was purchased from Sigma (St. Louis, Mo.). Folate-saporin was prepared following folate-protein conjugation methods published by Leamon and Low in The Journal of Biological Chemistry 1992, 267(35); 24966-24971. Briefly, folic acid was dissolved in DMSO and incubated with a 5 fold molar excess of 1-ethyl-3-(3-dimethylaminopropyl)carbodiimide for 30 minutes at room temperature. The saporin was dissolved in 100 mM $KH_2PO_4$, 100 mM boric acid, pH 8.5. A 10-fold molar excess of the "activated" vitamin was added to the protein solution and the labeling reaction was allowed to proceed for 4 hours. Unreacted material was separated from the labeled protein using a Sephadex G-25 column equilibrated in phosphate-buffered saline, pH 7.4.

EXAMPLE 22

Synthesis of Folate-Momordin and Folate-Gelonin

The proteins momordin and gelonin were purchased from Sigma (St. Louis, Mo.). Folate-cys pyridyldisulfide was prepared by reacting folate-cys with Aldrithiol (Sigma, St. Louis, Mo.). Both proteins were dissolved in 0.1M HEPPS buffer, pH 8.2. A 6-fold molar excess of Trouts reagent (Aldrich St. Louis, Mo.) dissolved in DMSO (16 mM) was added to each protein solution. The solutions were allowed to react for 1 hour at room temperature. Unreacted material was separated from the protein using a Sephadex G-25 column equilibrated in 0.1M phosphate buffer, pH 7.0. Ellmans test for the presence of free thios were positive for both proteins. While the protein solution was on ice, a 5-fold molar excess of folate-cys pyridyldisulfide dissolved in DMSO was added. The resulting solution was warmed up to room temperature and reacted for 30 minutes. Unreacted material was separated from the labeled protein using a Sephadex G-25 column equilibrated in phosphate-buffered saline, pH 7.4.

EXAMPLE 23

Preparation of Folate-Targeted Clodronate or Prednisolone Phosphate Liposomes Liposomes were prepared following methods by Leamon et al. in *Bioconjugate Chemistry* 2003, 14; 738-747. Briefly, lipids and cholesterol were purchased from Avanti Polar Lipids (Alabaster, Ala.). Folate-targeted liposomes consisted of 40 mole % cholesterol, 5 mole % polyethyleneglycol (Mr~2000)-derivatized phosphatidylethanolamine (PEG2000-PE, Nektar Ala., Huntsville, Ala.), 0.03 mole % folate-cysteine-PEG3400-PE and 54.97 mole % egg phosphatidylcholine. Lipids in chloroform were dried to a thin film by rotary evaporation and then rehydrated in PBS containing either clodronate (250 mg/ml) or prednisolone phosphate (100 mg/ml). Rehydration was accomplished by vigorous vortexing followed by 10 cycles of freezing and thawing. Liposomes were then extruded 10 times through a 50 nm pore size polycarbonate membrane using a high-pressure extruder (Lipex Biomembranes, Vancouver, Canada). The liposomes were separated from unencapsulated clodronate or prednisolone phosphate by passage through a CL4B size exclusion column (Sigma, St. Louis, Mo.) in PBS. Average particle size was between 70 and 100 nm.

EXAMPLE 24

Folate-FITC Binding to Human Monocytes

Folate-FITC binding to human monocytes and to human monocytes preincubated with a 100-fold excess of unlabeled folic acid was measured. Peripheral blood monocytes were isolated as described in Examples 14 and 15 and folate-FITC binding and flow cytometry were performed as described in Example 16. As shown in FIG. 1, folate-FITC bound to human peripheral blood monocytes in the absence of unlabeled folic acid and binding was competed in the presence of a 100-fold excess of unlabeled folic acid.

EXAMPLE 25

Folate-FITC Binding to Cd11b$^+$ Human Monocytes

Figure 2:
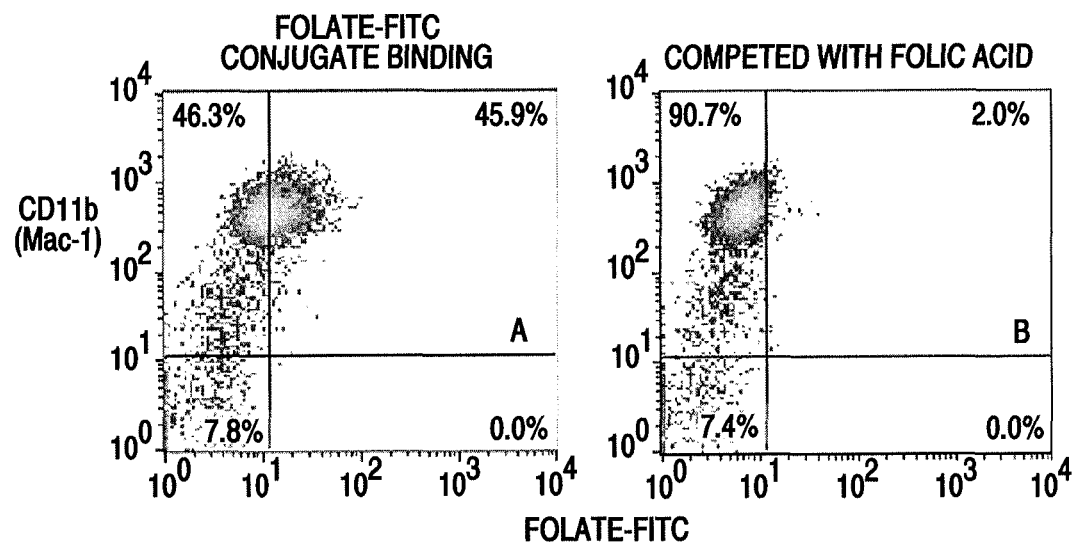
FIG. 2 shows folate-fluorescein (folate-FITC e.g. folate-fluorescein isothiocyanate) binding, quantified by flow cytometry, to CD11b+ human monocytes (panel A) and to CD11b+ human monocytes preincubated with an excess of unlabeled folic acid (panel B) to compete with folate-FITC for binding.

Folate-FITC binding to CD11b$^+$ human monocytes and to CD11b$^+$ human monocytes preincubated with a 100-fold excess of unlabeled folic acid was quantified. Peripheral blood monocytes were isolated as described in Examples 14 and 15 and folate-FITC binding and flow cytometry were performed as described in Example 16. As shown in FIG. 2, folate-FITC bound to 45.9% of human peripheral blood monocytes in the absence of unlabeled folic acid and to 2% of human peripheral blood monocytes in the presence of a 100-fold excess of unlabeled folic acid.

EXAMPLE 26

Binding to Human Monocytes of Folate-FITC and Antibodies to CD Markers

Figure 3:
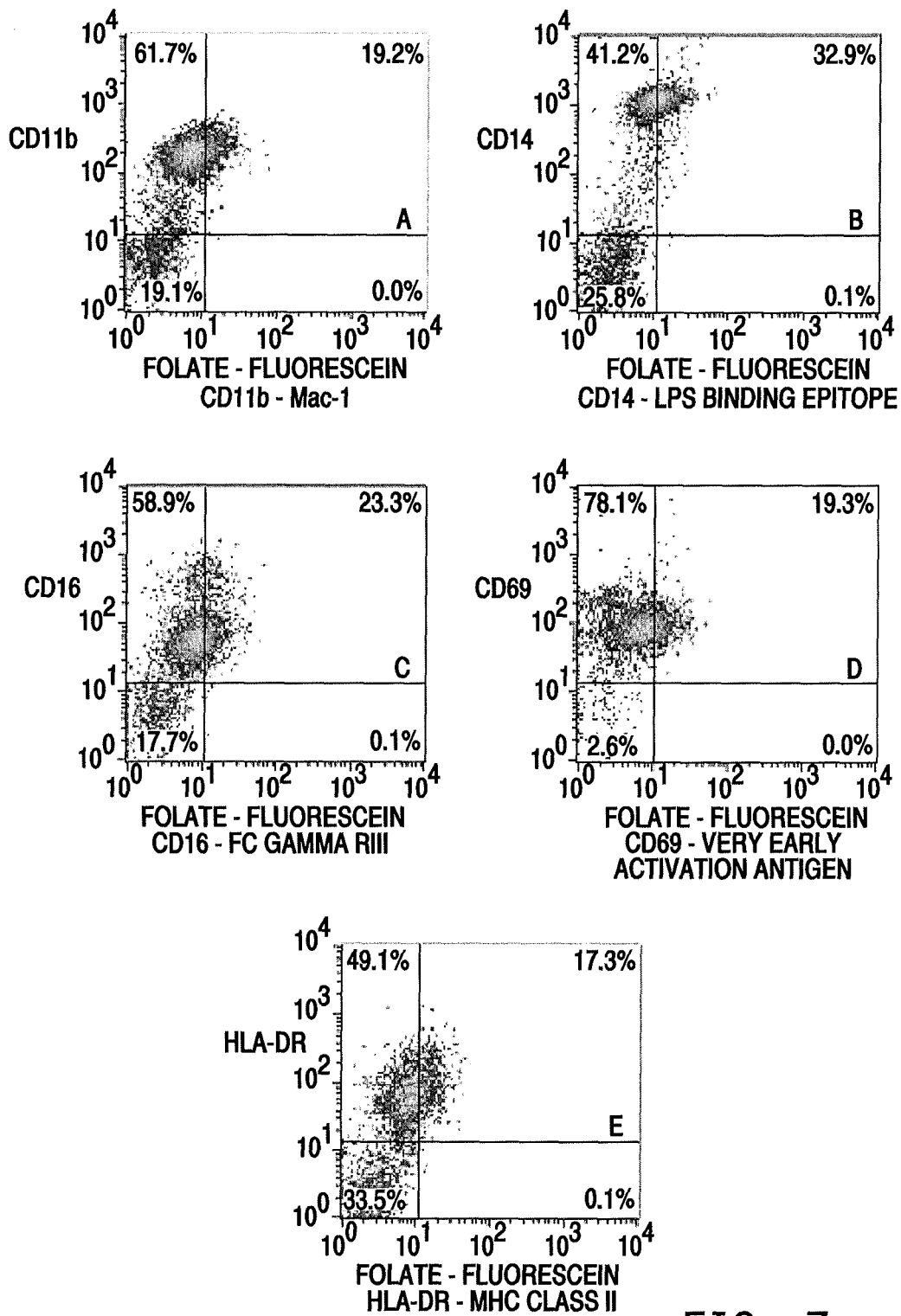
FIG. 3 shows flow cytometry analysis, using CD11b (A), CD14 (B), CD 16 (C), CD69 (D), and HLA-DR (E) antibodies, of CD markers that are co-expressed with the folate receptor on human monocytes.

Folate-FITC binding and binding of antibodies to CD11b, CD14, CD16, CD69, and HLA-DR markers on human monocytes was quantified. Peripheral blood monocytes were isolated as described in Examples 14 and 15 and folate-FITC and antibody binding and flow cytometry were performed as described in Example 16. As shown in FIG. 3, CD11b, CD14, CD16, CD69, and HLA-DR markers are co-expressed with the folate receptor on human peripheral blood monocytes. It has been reported that CD 14- and CD16-expressing monocytes are a population of proinflammatory monocytes (Weber et al., *J. Leuk. Biol.*, 67:699-704 (2000) and Ziegler-Heitbrock, *J. Leuk. Biol.*, 67:603-606 (2000)) suggesting that the folate-receptor-expressing monocytes (about 2% of total circulating white blood cells) are proinflammatory monocytes.

EXAMPLE 27

Figure 4:
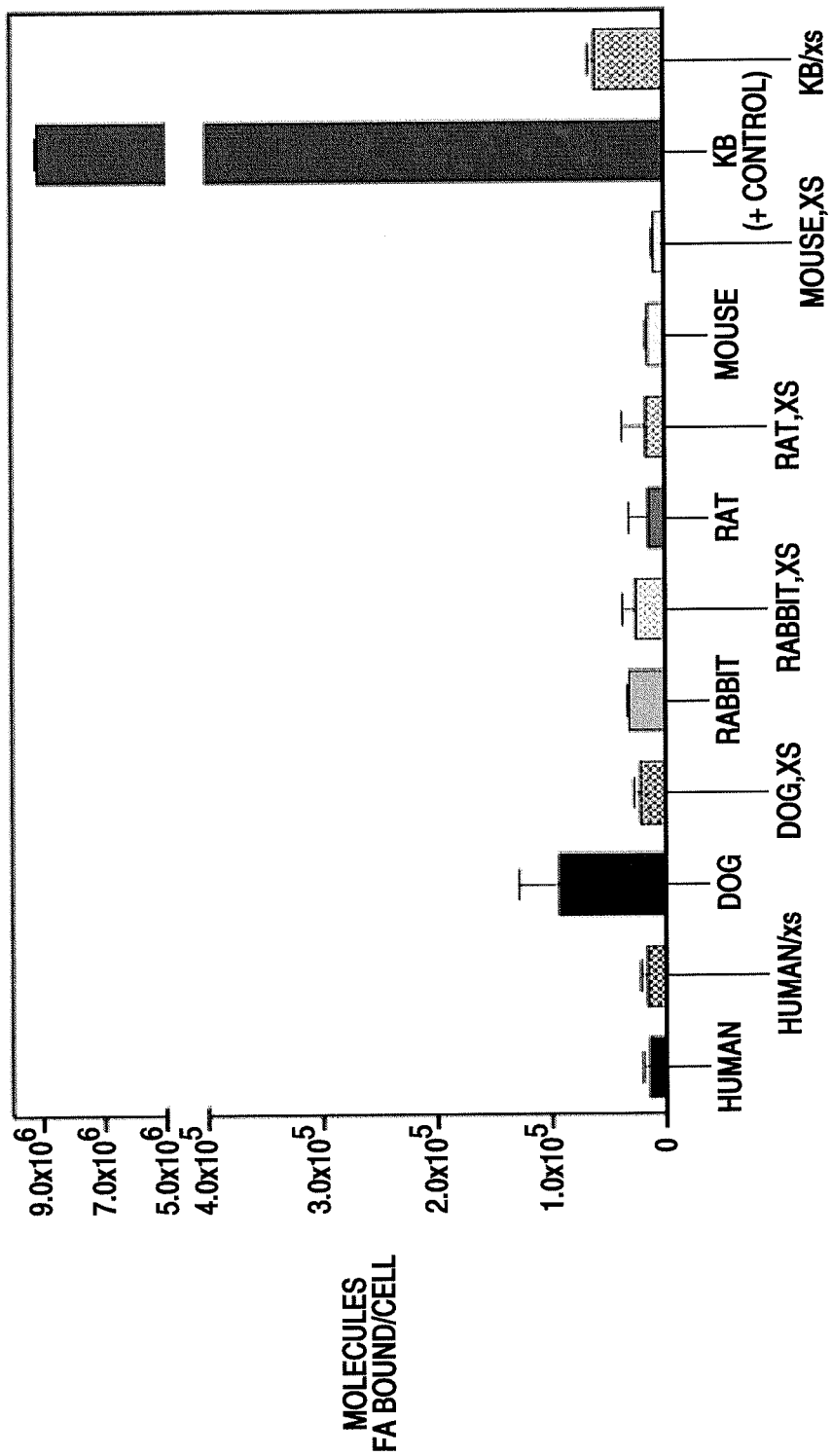
FIG. 4 shows binding of $^3$H-folic acid to white blood cells from humans, dogs, rabbits, rats, mice, or to KB cells. The cells were either preincubated with a 100-fold excess of unlabeled folic acid (cross-hatched bars labeled with an "xs") or not preincubated with excess unlabeled folic acid (solid bars).

Binding of $^3$H-Folic Acid to White Blood Cells $^3$H-Folic acid binding to white blood cells was quantified as described in Example 16. White blood cells were preincubated with a 100-fold excess of unlabeled folic acid for the samples labeled "xs." As shown in FIG. 4, folate receptors are detectable on white blood cells from dogs and mice and on KB cells.

EXAMPLE 28

Folate-FITC Binding to Peripheral Blood Monocytes from Dogs and Horses

Figure 5:
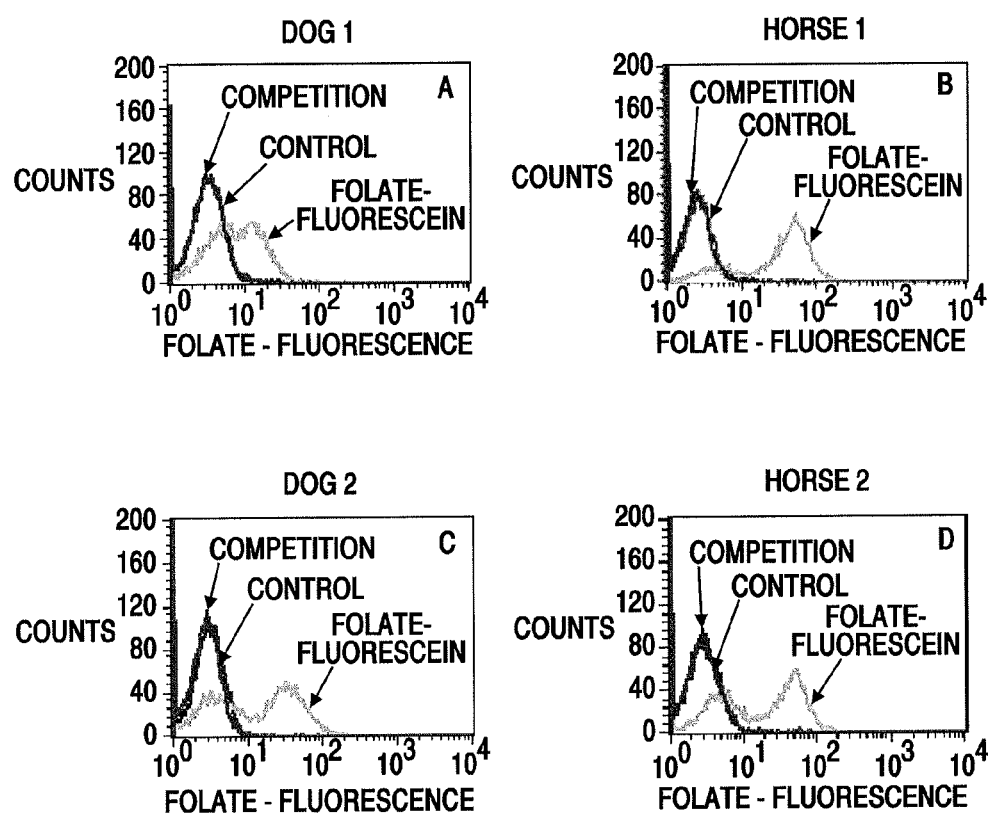
FIG. 5 shows folate-FITC binding, analyzed by flow cytometry, to peripheral blood monocytes from dogs (panels A and C) and horses (panels B and D) and competition of binding by unlabeled folic acid.

Folate-FITC binding to peripheral blood monocytes from dogs and horses was quantified for monocytes preincubated or not preincubated with a 100-fold excess of unlabeled folic acid. Peripheral blood monocytes were isolated as described in Examples 14 and 15 and folate-FITC binding and flow cytometry were performed as described in Example 16. As shown in FIG. 5, folate receptors were detectable on peripheral blood monocytes of both dogs and horses.

EXAMPLE 29

Figure 6:
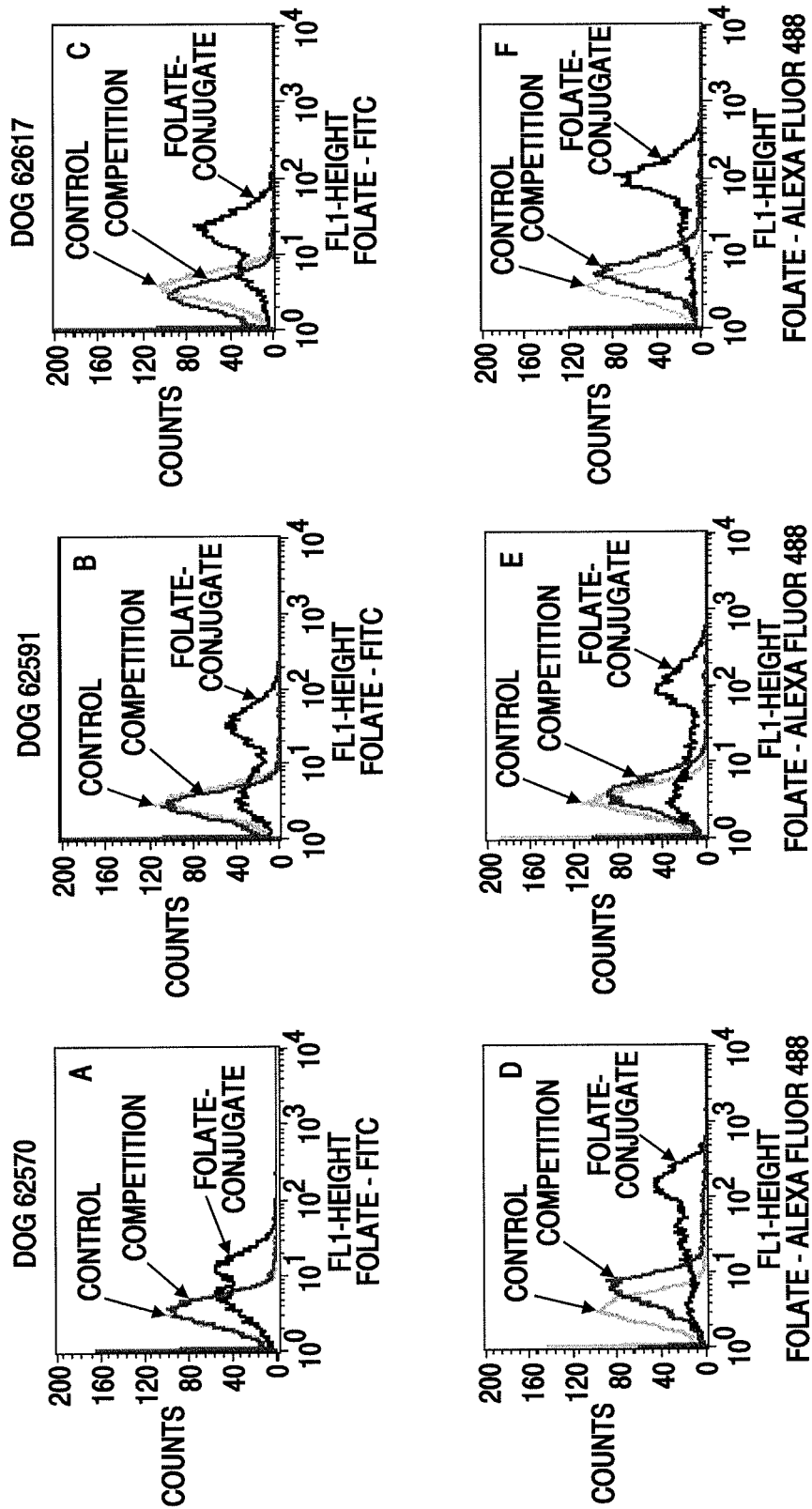
FIG. 6 shows folate-FITC (A-C) or folate-AlexaFluor 488 (D-F) binding, analyzed by flow cytometry, to peripheral blood monocytes from dogs and competition of binding by unlabeled folic acid.

Folate-FITC or Folate-Alexafluor 488 Binding to Peripheral Blood Monocytes from Dogs Folate-FITC binding or folate-AlexaFluor 488 binding to peripheral blood monocytes from dogs was quantified for monocytes preincubated or not preincubated with a 100-fold excess of unlabeled folic acid. Peripheral blood monocytes were isolated as described in Examples 14 and 15 and folate-FITC and folate-AlexaFluor 488 binding and flow cytometry were performed as described in Example 16. As shown in FIG. 6, folate receptors were detectable on peripheral blood monocytes of dogs using either folate-FITC or folate-AlexaFluor 488.

EXAMPLE 30

Folate-Phycoerythrin Binding to Human Peripheral Blood Monocytes

Figure 7:
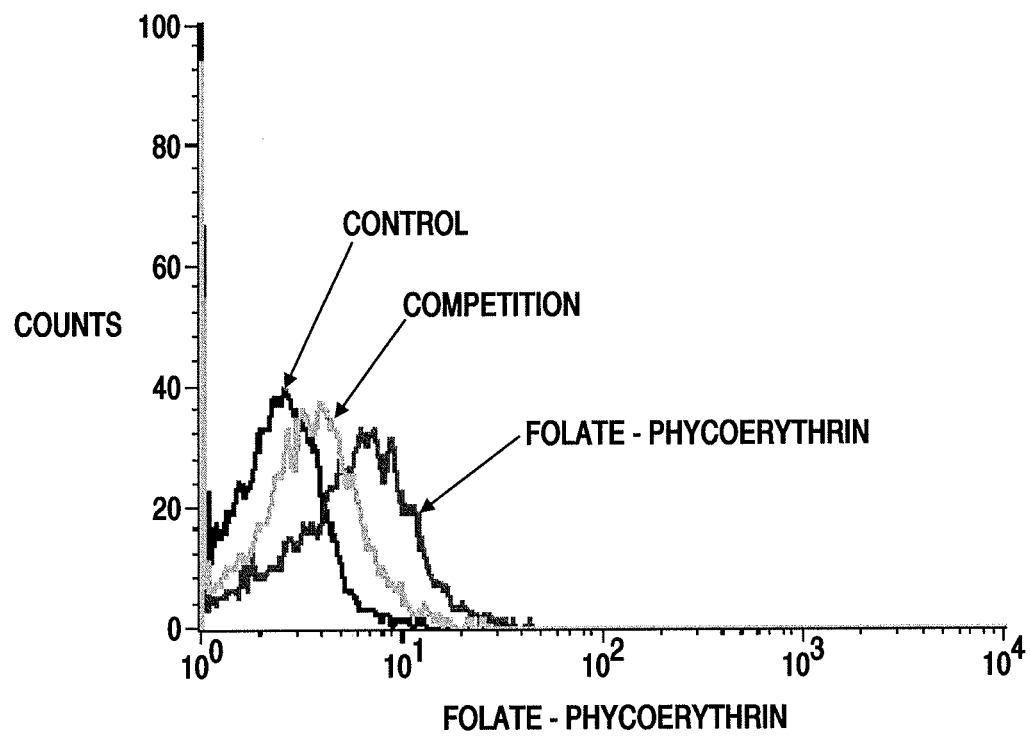
FIG. 7 shows folate-phycoerythrin binding, analyzed by flow cytometry, to human peripheral blood monocytes and competition by unlabeled folic acid.

Folate-phycoerythrin binding to human peripheral blood monocytes was quantified for monocytes preincubated or not preincubated with a 100-fold excess of unlabeled folic acid. Peripheral blood monocytes were isolated as described in Examples 14 and 15 and folate-phycoerythrin binding and flow cytometry were performed as described in Example 16. As shown in FIG. 7, folate receptors were detectable on human peripheral blood monocytes using folate-phycoerythrin.

EXAMPLE 31

Figure 8:
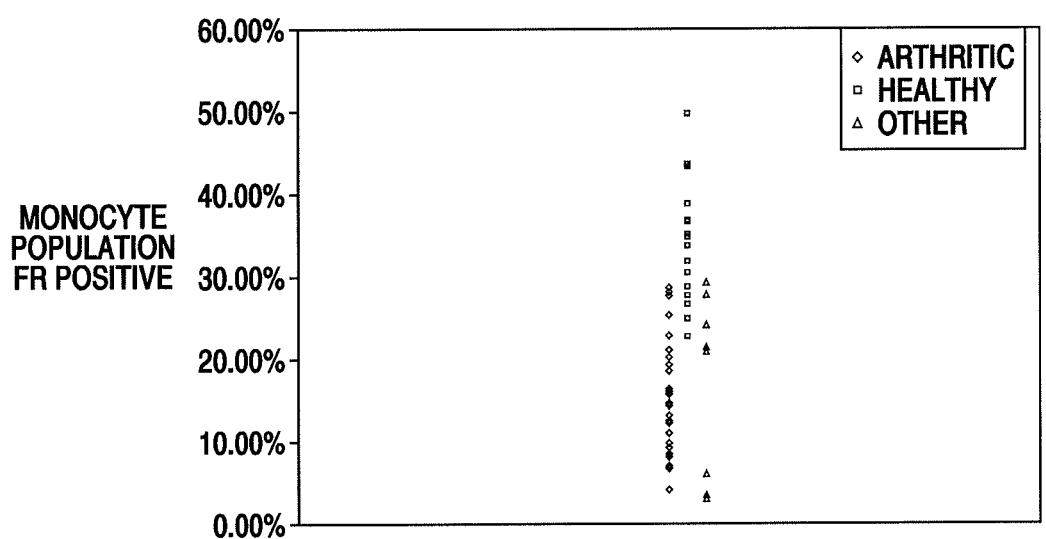
FIG. 8 shows the percentage of human peripheral blood monocytes that are folate receptor positive in healthy humans (squares) and in patients with rheumatoid arthritis (diamonds), osteoarthritis (upper group of triangles), and fibromyalgia (three triangles at lowest percentages).

Folate-FITC Binding to Peripheral Blood Monocytes from Healthy Humans and Patients with Arthritis or Fibromyalgia Folate-FITC binding to peripheral blood monocytes from healthy humans (squares) and from patients with rheumatoid arthritis (diamonds), osteoarthritis (upper group of triangles), and fibromyalgia (three triangles at lowest percentages) was quantified. Peripheral blood monocytes were isolated as described in Examples 14 and 15 and folate-FITC binding and flow cytometry were performed as described in Example 16. As shown in FIG. 8, folate receptors were detectable on peripheral blood monocytes of humans using folate-FITC. In this assay, patients with fibromyalgia appear to have lower percentages of folate-receptor expressing monocytes in peripheral blood than healthy individuals. The difference may be due to differentiation of monocytes into macrophages and to the egress of activated macrophages from the circulation and localization of activated macrophages to sites of inflammation. Regardless of the reason for this difference, the results in FIG. 8 suggest that folate-imaging agent conjugates may be useful in diagnosing monocyte-mediated disease states, and that one such monocyte-mediated disease state may be fibromyalgia.

EXAMPLE 32

Animal Model of Arthritis

Arthritis was induced in 150-200 g female Lewis rats (Harlan, Indianapolis, Ind.), n=2-5/dose group. Briefly, 0.5 mg of heat-killed *Mycoplasma butericum*, suspended in mineral oil (5 mg/ml), was injected on day 0 into the left hind foot of rats following anesthesia with ketamine and xylazine. All treated animals developed arthritis, as evidenced by dramatic swelling in the injected paw, progressive swelling in all noninjected limbs due to the systemic progression of arthritis, and radiographic analysis of affected limbs. All rats were maintained on a folate-deficient diet (DYETS, Inc., Bethlehem, Pa.) for 3 weeks prior to administration of therapeutic agents in order to lower serum folate levels to physiologically relevant concentrations. Control rats were also maintained on a folate-deficient diet but were not induced to develop arthritis.

EXAMPLE 33

Effect of Therapeutic Agents on Adjuvant-Induced Arthritis

Figure 9:
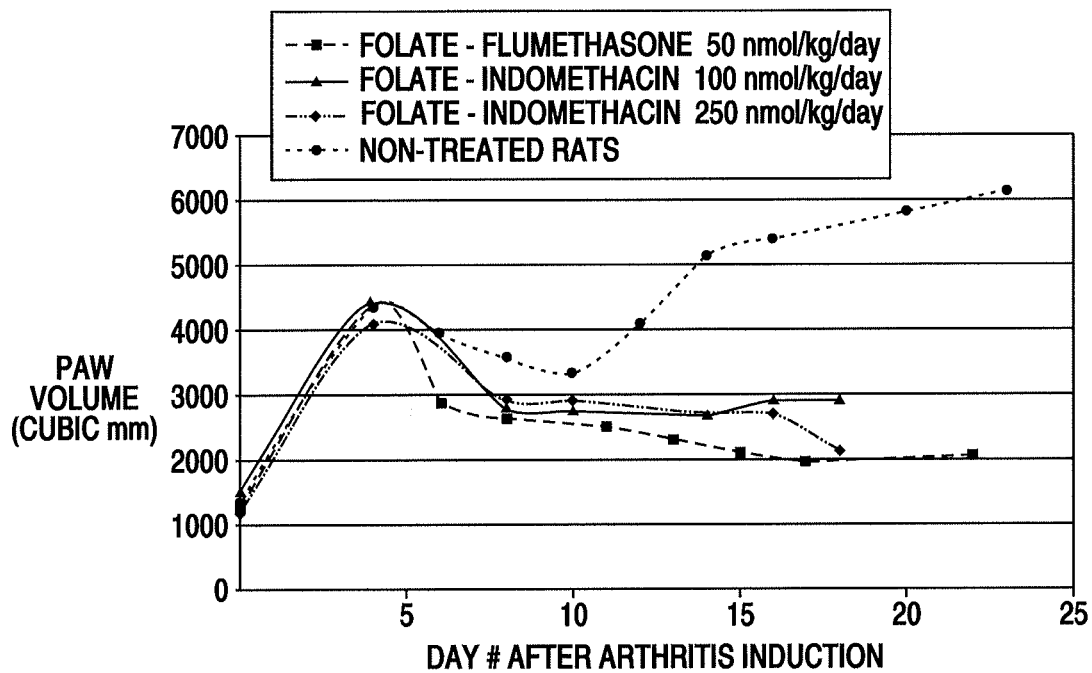
FIG. 9 shows paw volume over time in rats after arthritis induction. The rats were treated with folate-flumethasone (50 nmoles/kg/day; squares) or folate-indomethacin (100 (triangles) or 250 (diamonds) nmoles/kg/day) or were untreated (circles).

The protocol described in Example 32 for arthritis induction was followed. The efficacy of folate-flumethasone (50 nmoles/kg/day) and folate-indomethacin (100 or 250 nmoles/kg/day) against adjuvant-induced arthritis in rats was investigated. Rats were injected intraperitoneally with either saline (control rats) or folate-flumethasone (50 nmoles/kg/day) or folate-indomethacin (100 or 250 nmoles/kg/day) starting at day 4. Calipers were used to measure left foot dimensions on the days indicated in FIG. 9. The sudden increase in swelling of the adjuvant-injected foot is due to influx of neutrophils which have no folate receptors. Consequently, the therapy has no impact on this phase of paw swelling. However, the data in FIG. 9 suggests that after about 7 days folate-flumethasone and folate-indomethacin have potent therapeutic effects in this adjuvant-induced arthritis model by eliminating or inactivating monocytes as a result of binding and internalization by monocytes of folate-flumethasone or folate-indomethacin.

EXAMPLE 34

Folate-FITC Binding to Peripheral Blood Monocytes from Patients with Arthritis

Figure 10:
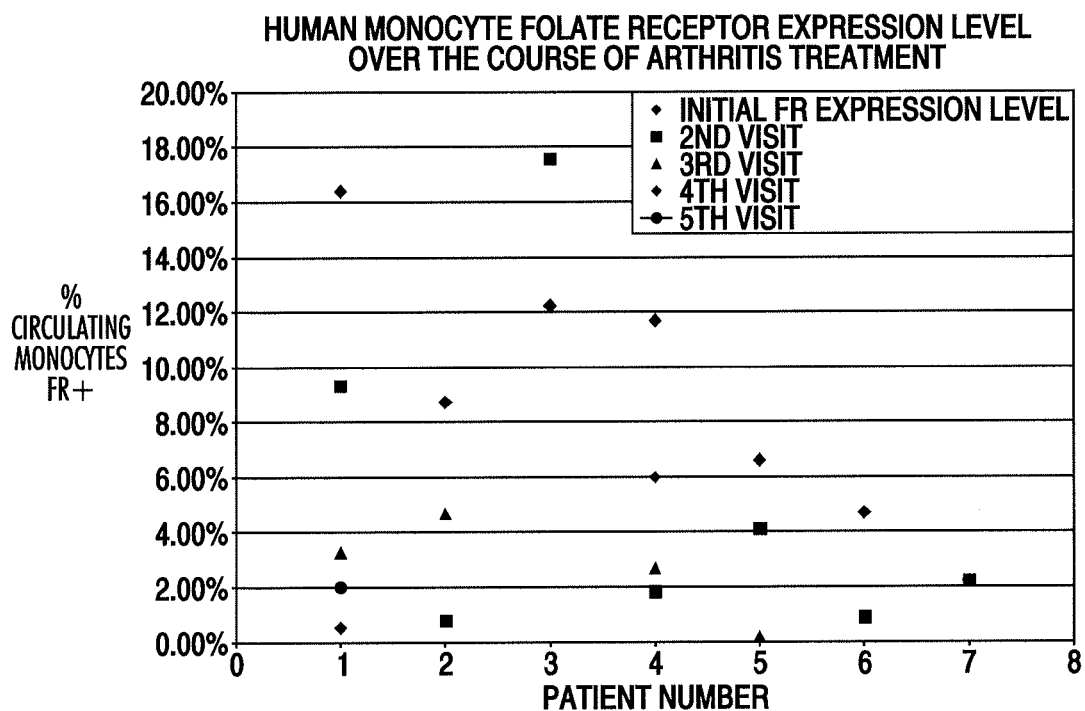
FIG. 10 shows the percentage of human peripheral blood monocytes that are folate receptor positive in patients with rheumatoid arthritis over the course of therapy.

Folate-FITC binding to peripheral blood monocytes from patients with rheumatoid arthritis was quantified. Peripheral blood monocytes were isolated as described in Examples 14 and 15 and folate-FITC binding and flow cytometry were performed as described in Example 16. As shown in FIG. 10, folate receptors were detectable on peripheral blood monocytes of humans by using folate-FITC. Patient #1 (x-axis shows patient #) was treated with Enbrel/methotrexate, patient #2 was treated with methotrexate, patient #3 was treated with Medrol, patient #4 was treated with Methotrexate/Azulfidine/Plaquenil, Ibuprofen, prednisone, patient #5 was treated with Methotrexate/Azulfidine/Plaquenil, Celebrex, Medrol, patient #6 was treated with Methotrexate/Azulfidine/Plaquenil, Celebrex, prednisone, and patient #7 was treated with Plaquenil, Arava. In this assay, the percentage of folate-receptor expressing monocytes in peripheral blood of patients with arthritis decreased over the course of arthritis therapy. The results in FIG. 10 indicate that folate receptor-expressing monocytes contribute to the pathogenesis of arthritis.

The foregoing exemplified embodiments are intended to be illustrative of the invention described herein, and should not be construed as limiting. It is to be understood that several variations of those embodiments are contemplated, and are intended to be included herein.

Illustratively, in each of Examples 2 through 13, a wide variety of folate analogs and derivatives may be substituted for folate itself in forming the folate linker conjugates. Those analogs and derivatives, or protected forms thereof, may be included in the synthetic protocols described herein. In addition, structural modifications of the linker portion of the conjugates is contemplated herein. For example, a number of amino acid substitutions may be made to the linker portion of the conjugate, including but not limited to naturally occurring amino acids, as well as those available from conventional synthetic methods. In one aspect, beta, gamma, and longer chain amino acids may be used in place of one or more alpha amino acids. In another aspect, the stereochemistry of the chiral centers found in such molecules may be selected to form various mixture of optical purity of the entire molecule, or only of a subset of the chiral centers present. In another aspect, the length of the peptide chain included in the linker may be shortened or lengthened, either by changing the number of amino acids included therein, or by including more or fewer beta, gamma, or longer chain amino acids. In another aspect, the selection of amino acid side chains in the peptide portion may be made to increase or decrease the relative hydrophilicity of the linker portion specifically, or of the overall molecule generally.

Similarly, the length and shape of other chemical fragments of the linkers described herein may be modified. In one aspect, where the linker includes an alkylene chain, such as is found in Examples 3, 4, and 7, the alkylene may be longer or shorter, or may include branched groups, or include a cyclic portion, which may be in line or Spiro relative to the alkylene chain. In another aspect, where the linker includes a beta thiol releasable fragment, such as the thioethyloxy bivalent fragment in Examples 8 through 13, it is appreciated that other intervening groups connecting the thiol end to the hydroxy or carbonate end may be used in place of the ethylene bridge, such as but not limited to optionally substituted benzyl groups, where the hydroxy end is connected at the benzyl carbon and the thiol end is connected through the ortho or para phenyl position, and vice versa.

In another illustrative embodiment, structural modifications may be made to the linker to include additional releasable linkers, such as those described in U.S. Patent Application Publication No. 2005/0002942.

What is claimed is:
1. A method for imaging osteoarthritis, the method comprising the step of:
    administering to a patient suffering from the osteoarthritis an effective amount of a composition comprising a conjugate comprising $A_b$ linked to X,
    wherein $A_b$ comprises a folate and X comprises an imaging agent.
2. The method of claim 1 wherein X comprises a metal chelating moiety.

3. The method of claim 2 wherein X further comprises a metal cation.

4. The method of claim 3 wherein the metal cation is a radionuclide.

5. The method of claim 4 wherein the radionuclide is selected from the group consisting of technetium, gallium, indium, and a positron emitting radionuclide.

6. The method of claim 1 wherein X comprises a fluorophore.

7. The method of claim 6 wherein the fluorophore comprises a compound selected from the group consisting of fluorescein, Oregon Green, rhodamine, phycoerythrin, Cy3, Cy5, Cy7, and Texas Red.

8. The method of claim 7 wherein the fluorophore is fluorescein.

9. The method of claim 6 wherein the fluorophore is a long wavelength fluorescent dye.

10. The method of any one of claims 1 to 5 wherein $A_b$ is folate.

11. The method of claim 1 wherein the composition is in a parenteral dosage form.

12. The method of claim 11 wherein the parenteral dosage form is selected from the group consisting of intradermal, subcutaneous, intramuscular, intraperitoneal, intravenous, and intrathecal dosage forms.

13. The method of claim 1 wherein the composition is a reconstituted lyophilizate.

14. The method of claim 1 wherein the composition further comprises a pharmaceutically acceptable carrier.

15. The method of claim 14 wherein the pharmaceutically acceptable carrier is a liquid carrier.

16. The method of claim 15 wherein the liquid carrier is selected from the group consisting of saline, glucose, alcohols, glycols, esters, amides, and a combination thereof.

17. The method of claim 1 wherein the conjugate is administered at a dose ranging from about 1 ng/kg of patient body weight to about 1 mg/kg of patient body weight.

18. The method of claim 1 wherein the conjugate is administered at a dose ranging from about 1 µg/kg of patient body weight to about 100 µg/kg of patient body weight.

19. The method of claim 1 wherein the conjugate is administered at a dose ranging from about 1 µg/kg of patient body weight to about 500 µg/kg of patient body weight.

20. The method of claim 1 wherein the conjugate is administered in a single dose.

21. The method of claim 1 wherein the conjugate is administered in multiple doses.

22. The method of claim 1 wherein the patient is a human patient.

23. The method of claim 1 wherein the patient is a veterinary patient.

24. The method of claim 1 wherein the osteoarthritis is visualized by imaging.

* * * * *